(12) United States Patent
Madsen et al.

(10) Patent No.: US 8,887,911 B2
(45) Date of Patent: Nov. 18, 2014

(54) PACKAGES AND KITS FOR ANALYTE MONITORING DEVICES, AND METHODS RELATED THERETO

(71) Applicant: Abbott Diabetes Care Inc., Alameda, CA (US)

(72) Inventors: Arne Madsen, San Francisco, CA (US); Mark William Yadgir, Walnut Creek, CA (US); Linda Montoto, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 15 days.

(21) Appl. No.: 13/693,767

(22) Filed: Dec. 4, 2012

(65) Prior Publication Data

US 2013/0161213 A1 Jun. 27, 2013

Related U.S. Application Data

(60) Provisional application No. 61/568,832, filed on Dec. 9, 2011.

(51) Int. Cl.
*B65D 85/38* (2006.01)
*A61B 19/02* (2006.01)
(Continued)

(52) U.S. Cl.
CPC ............. *B65D 85/00* (2013.01); *B65D 5/48014* (2013.01); *A61J 1/16* (2013.01); *A61M 5/14* (2013.01); *B65D 5/5007* (2013.01); *G06F 19/3462* (2013.01); *A61B 5/14532* (2013.01)
USPC ....... 206/363; 206/305; 206/438; 229/120.18

(58) Field of Classification Search
CPC ............... B65D 5/326; B65D 5/48002; B65D 5/48014; A61J 1/00; A61B 5/14532; A61B 5/14546; A61B 10/0046; B01L 3/5085
USPC ......... 206/305, 363–365, 370, 438, 569–572, 206/232; 229/120.11, 120.18, 120.15; 422/530; 600/365
See application file for complete search history.

(56) References Cited

U.S. PATENT DOCUMENTS 306,620 A * 10/1884 Jaeger ....................... 229/120.18
348,924 A * 9/1886 Munson ................... 229/120.18

(Continued)

FOREIGN PATENT DOCUMENTS

EP 1044885 A1 * 10/2000

*Primary Examiner* — Bryon Gehman
(74) *Attorney, Agent, or Firm* — Edward J. Baba; Daniel G. Stoddard; Bozicevic, Field & Francis LLP

(57) ABSTRACT

Generally, packages for an analyte monitoring device are provided. The packages include a container for containing an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container. Analyte monitoring kits and methods relating thereto are also provided.

33 Claims, 16 Drawing Sheets

(51) Int. Cl.
  *B65D 25/04*   (2006.01)
  *B65D 5/48*    (2006.01)
  *B65D 85/00*   (2006.01)
  *A61M 5/14*    (2006.01)
  *B65D 5/50*    (2006.01)
  *A61J 1/16*    (2006.01)
  *G06F 19/00*   (2011.01)
  *A61B 5/145*   (2006.01)

(56) References Cited

U.S. PATENT DOCUMENTS

| | | | |
|---|---|---|---|
| 2,015,278 A * | 9/1935 | Meyer | 229/120.18 |
| 2,084,635 A * | 6/1937 | Friedrich et al. | 206/756 |
| 2,503,379 A * | 4/1950 | Davis | 229/120.18 |
| RE25,073 E * | 10/1961 | Phillips | 229/120.18 |
| 3,845,898 A * | 11/1974 | Hackenberg | 229/120.26 |
| 4,105,154 A * | 8/1978 | Meyers et al. | 229/120.18 |
| 4,545,382 A | 10/1985 | Higgins et al. | |
| 4,711,245 A | 12/1987 | Higgins et al. | |
| 5,143,210 A * | 9/1992 | Warwick et al. | 206/569 |
| 5,262,035 A | 11/1993 | Gregg et al. | |
| 5,262,305 A | 11/1993 | Heller et al. | |
| 5,264,104 A | 11/1993 | Gregg et al. | |
| 5,320,725 A | 6/1994 | Gregg et al. | |
| 5,356,786 A | 10/1994 | Heller et al. | |
| 5,361,898 A * | 11/1994 | Gottlieb | 229/120.18 |
| 5,429,243 A * | 7/1995 | Woelk et al. | 229/120.26 |
| 5,509,410 A | 4/1996 | Hill et al. | |
| 5,513,752 A * | 5/1996 | Gottlieb | 229/120.18 |
| 5,593,852 A | 1/1997 | Heller et al. | |
| 5,601,435 A | 2/1997 | Quy | |
| 5,628,890 A | 5/1997 | Carter et al. | |
| 5,820,551 A | 10/1998 | Hill et al. | |
| 5,822,715 A | 10/1998 | Worthingtin et al. | |
| 5,899,855 A | 5/1999 | Brown | |
| 5,918,603 A | 7/1999 | Brown | |
| 6,071,391 A | 6/2000 | Gotoh et al. | |
| 6,120,676 A | 9/2000 | Heller et al. | |
| 6,121,009 A | 9/2000 | Heller et al. | |
| 6,143,164 A | 11/2000 | Heller et al. | |
| 6,144,837 A | 11/2000 | Quy | |
| 6,161,095 A | 12/2000 | Brown | |
| 6,175,752 B1 | 1/2001 | Say et al. | |
| 6,270,455 B1 | 8/2001 | Brown | |
| 6,284,478 B1 | 9/2001 | Heller | |
| 6,299,757 B1 | 10/2001 | Feldman et al. | |
| 6,338,790 B1 | 1/2002 | Feldman et al. | |
| 6,377,894 B1 | 4/2002 | Deweese et al. | |
| 6,461,496 B1 | 10/2002 | Feldman et al. | |
| 6,503,381 B1 | 1/2003 | Gotoh et al. | |
| 6,514,460 B1 | 2/2003 | Fendrock | |
| 6,514,718 B2 | 2/2003 | Heller et al. | |
| 6,540,891 B1 | 4/2003 | Stewart et al. | |
| 6,560,471 B1 | 5/2003 | Heller et al. | |
| 6,591,125 B1 | 7/2003 | Buse et al. | |
| 6,592,745 B1 | 7/2003 | Feldman et al. | |
| 6,600,997 B2 | 7/2003 | Deweese et al. | |
| 6,616,819 B1 | 9/2003 | Liamos et al. | |
| 6,618,934 B1 | 9/2003 | Feldman et al. | |
| 6,676,816 B2 | 1/2004 | Mao et al. | |
| 6,730,200 B1 | 5/2004 | Stewart et al. | |
| 6,736,957 B1 | 5/2004 | Forrow et al. | |
| 6,746,582 B2 | 6/2004 | Heller et al. | |
| 6,749,740 B2 | 6/2004 | Liamos et al. | |
| 6,764,581 B1 | 7/2004 | Forrow et al. | |
| 6,773,671 B1 | 8/2004 | Lewis et al. | |
| 6,881,551 B2 | 4/2005 | Heller et al. | |
| 6,893,545 B2 | 5/2005 | Gotoh et al. | |
| 6,923,366 B2 * | 8/2005 | Lo Duca | 229/120.18 |
| 6,942,518 B2 | 9/2005 | Liamos et al. | |
| 7,041,468 B2 | 5/2006 | Drucker et al. | |
| 7,167,818 B2 | 1/2007 | Brown | |
| 7,299,082 B2 | 11/2007 | Feldman et al. | |
| 8,137,618 B2 * | 3/2012 | Zocchi | 600/365 |
| 2004/0020977 A1 * | 2/2004 | Lo Duca | 229/120.18 |
| 2004/0186365 A1 | 9/2004 | Jin et al. | |
| 2006/0025662 A1 | 2/2006 | Buse et al. | |
| 2006/0091006 A1 | 5/2006 | Wang et al. | |
| 2007/0068807 A1 | 3/2007 | Feldman et al. | |
| 2007/0095661 A1 | 5/2007 | Wang et al. | |
| 2007/0108048 A1 | 5/2007 | Wang et al. | |
| 2007/0199818 A1 | 8/2007 | Petyt et al. | |
| 2008/0066305 A1 | 3/2008 | Wang et al. | |
| 2008/0102441 A1 | 5/2008 | Chen et al. | |
| 2008/0148873 A1 | 6/2008 | Wang | |
| 2008/0267823 A1 | 10/2008 | Wang et al. | |
| 2009/0095625 A1 | 4/2009 | Forrow | |
| 2009/0255811 A1 | 10/2009 | Forrow et al. | |
| 2010/0198034 A1 | 8/2010 | Thomas et al. | |
| 2010/0325868 A1 | 12/2010 | Wang et al. | |

* cited by examiner

PACKAGES AND KITS FOR ANALYTE MONITORING DEVICES, AND METHODS RELATED THERETO

CROSS-REFERENCE TO RELATED APPLICATIONS

Pursuant to 35 U.S.C. §119(e), this application claims priority to U.S. Provisional Patent Application No. 61/568,832 filed on Dec. 9, 2011, the disclosure of which is herein incorporated by reference in its entirety.

BACKGROUND

Patients, such as diabetic patients, often use glucose monitoring devices to monitor their blood glucose levels. These glucose monitoring devices are typically packaged before ending up in possession of the patients or users of the devices. Patients often require additional products for their treatment or therapy of their diabetic condition. For example, patients may need to acquire and use a lancing device, lancets for the lancing device, test strips, etc. Furthermore, related product materials may also be given to patients. These products are typically packaged separately and often need to be acquired at different times and/or locations by the patient. Moreover, providing all products and accompanying product materials at one time to a patient, whether separately or clumped within a bag or box, can be disorganized and not user-friendly.

SUMMARY

In some aspects of the present disclosure, a package for an analyte monitoring device is provided. The package includes a container for containing an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container.

In some aspects of the present disclosure, an analyte monitoring kit is provided. The analyte monitoring kit includes a package for an analyte monitoring device. The package includes a container for containing an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container. The kit also includes an analyte monitoring device disposed in the container.

In some aspects of the present disclosure, a method of making a package for an analyte monitoring device is provided. The method includes providing a sheet of material, and generating a first cutout from the sheet of material. The shape of the first cutout is such that when folded in a plurality of locations, a container is formed. The method also includes folding the first cutout in a plurality of location to form a container for an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container.

INCORPORATION BY REFERENCE

The following patents, applications and/or publications are incorporated herein by reference for all purposes: U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/0198034; and U.S. provisional application No. 61/149,639 titled "Compact On-Body Physiological Monitoring Device and Methods Thereof", the disclosures of each of which are incorporated herein by reference in their entirety.

The following patents, applications and/or publications are also incorporated herein by reference for all purposes: U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. No. 6,616,819; U.S. Pat. No. 6,143,164; U.S. Pat. No. 6,592,745; U.S. Pat. No. 6,071,391 and U.S. Pat. No. 6,893,545; the disclosures of each of which are incorporated by reference herein in their entirety.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

DETAILED DESCRIPTION

Figure 1:
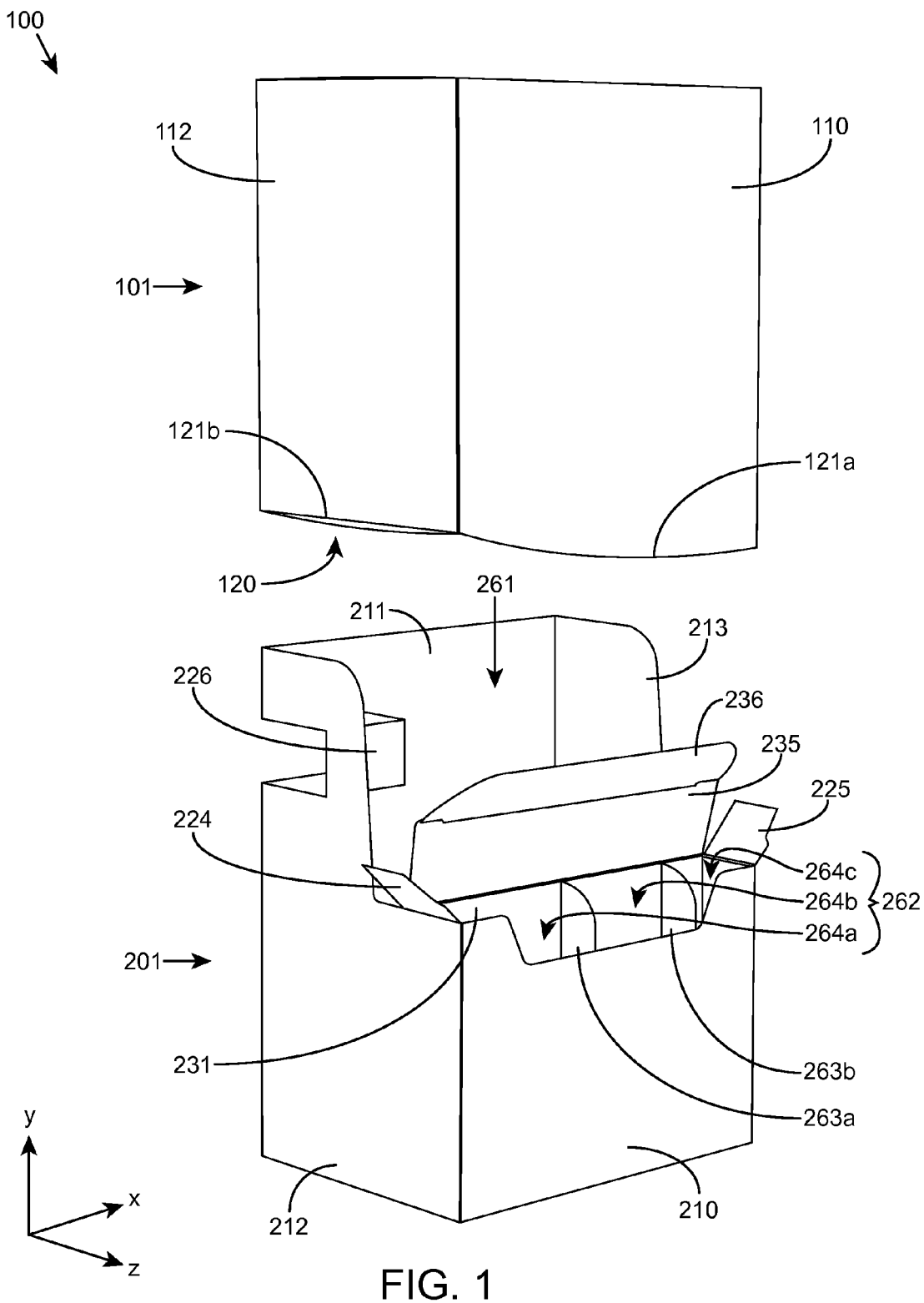
FIG. 1 illustrates a front perspective view of an analyte monitoring device package including a cover and container, with the cover removed from the container, according to one embodiment.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. Merely by way of example, the present disclosure is not limited to particular analytes, bodily or tissue fluids, blood or capillary blood, or sensor constructs or usages, unless implicitly or explicitly understood or stated otherwise, as such may vary. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

Patients, such as diabetic patients, may require an analyte monitoring device to monitor and/or treat their condition. Analyte monitoring devices may include, for example, glucose monitoring devices, such as glucose meters, and or other analyte monitoring devices that monitor or measure ketone bodies. Often patients require one or more additional products to help monitor or treat their condition. For example, a diabetic patient may require test strips, lancets, lancing devices, control solutions, medication, medication delivery devices, etc. These products are typically provided to the patient separately and/or at different times. Furthermore, the products may be accompanied with additional product-related materials, such as carrying cases and literature related to the product—e.g., manuals, warranty cards, logbooks, flyers, etc. Provided in the present disclosure are packages for an analyte monitoring device, and kits including an analyte monitoring device as well as one or more products or product materials to accompany the analyte monitoring device. Also provided in the present disclosure are methods related to the packages and kits.

FIGS. 1-11 provide example embodiments of packages for an analyte monitoring device, analyte monitoring kits including such packages, and related components thereof (e.g., ancillary containers), of the present disclosure. FIGS. 1-11 use reference numerals consistently to designate like parts, and thus the following descriptions may be applicable to more than one of the figures. Furthermore, for the sake of clarity and brevity, every reference number for objects illustrated in multiple figures are not repeated in every figure, and reference to the other figures may be made.

To facilitate explanation, an x-axis, y-axis, and z-axis are provided in some figures. The y-axis is used herein to refer generally to the vertical axis, which may be used in determining the top, bottom, height, etc., of the package, container, cover, kit, or component thereof. Also, references to "upward" are used herein to refer generally to the direction of the positive y-axis. Similarly, references to "downward" may be used herein to refer generally to the direction of the negative y-axis. Moreover, references to the longitudinal axis of the package, container, cover, kit, or component thereof, may be used herein and correspond generally to the y-axis. In some figures, an axis may be represented by a circle with dot inside of it, indicating the positive direction orthogonally out of the plane of the paper. In some figures an axis may be represented by a circle with an "X" inside of it, indicating the positive direction orthogonally into the plane of the paper.

Furthermore, references may be made herein to folding a sheet of material "inward", and represent folding the sheet of material out of the plane of the paper ("inward" toward the viewpoint of the "viewer"). Similarly, references may be made herein to folding a sheet of material "outward", and represent folding the sheet of material into the plane of the paper ("outward" away from the viewpoint of the "viewer").

As summarized above, in some aspects of the present disclosure, a package for an analyte monitoring device is provided. The package includes a container for containing an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container.

Any of the various analyte monitoring device may be disposed in the package. Example analytes that the device may monitor may include glucose and/or ketone bodies. For example, in one embodiment, the analyte monitoring device is a glucose monitoring device (e.g., glucose meter), such as glucose monitoring devices configured to work with analyte test strips available from Abbott Diabetes Care Inc., Alameda, Calif., e.g., FreeStyle® and FreeStyle Lite® glucose monitoring test strips.

Figure 2:
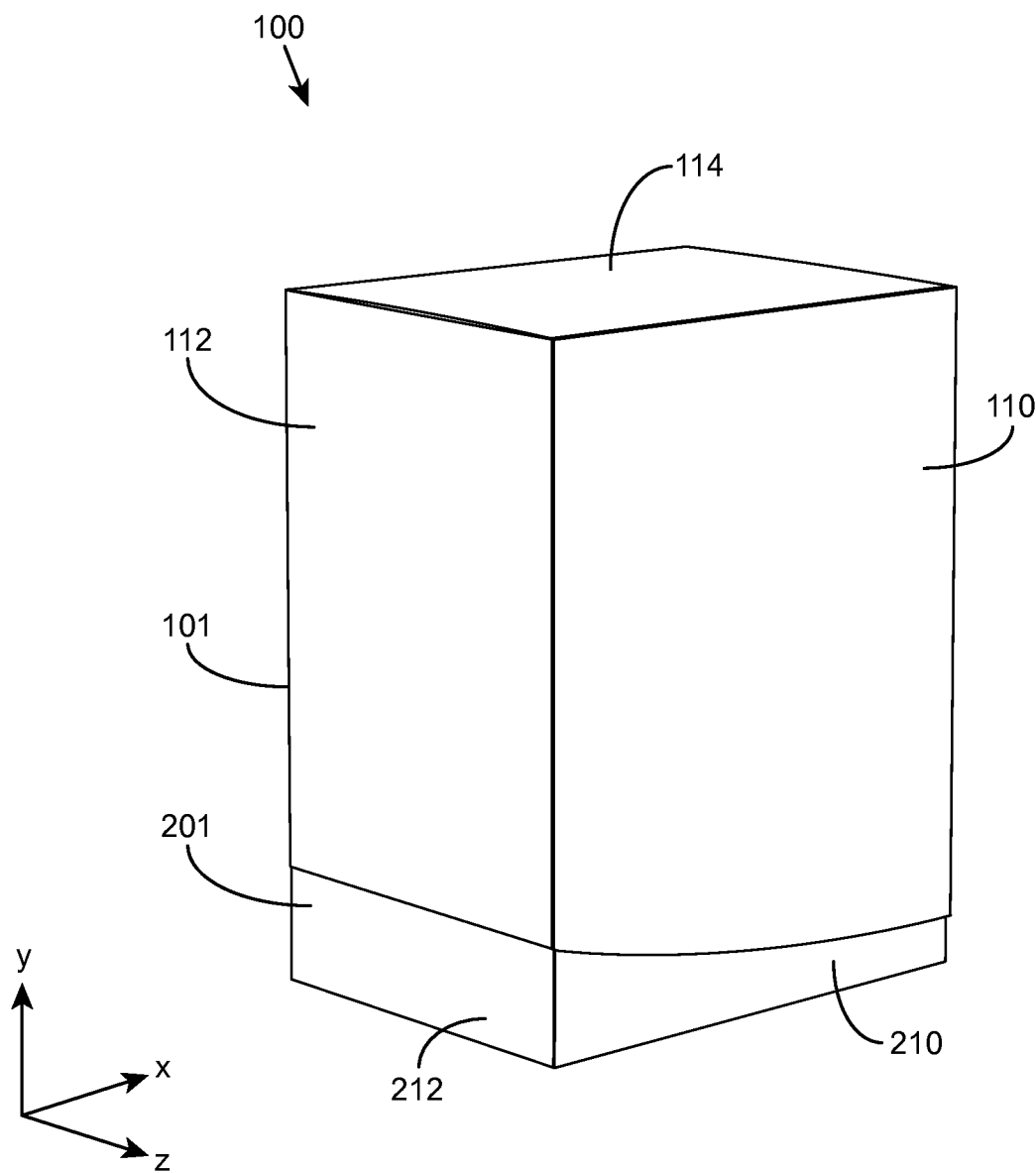
FIG. 2 illustrates a front perspective view of the analyte monitoring device package shown in FIG. 1 with the cover disposed on the container.

FIG. 1 illustrates a front perspective view of an analyte monitoring device package with the cover removed from the container, according to one embodiment. The package 100 in the embodiment shown includes a container 201 and a cover 101 that receives the container 201. The cover 101 is shown removed from the container 201. To cover the container 201, the cover 101 is placed over the container 201—e.g., by moving the cover 101 downward in the negative y-direction to receive the top end of the container 201. FIG. 2 illustrates a front perspective view of the analyte monitoring device package shown in FIG. 1 with the cover disposed on the container.

Figure 3A:
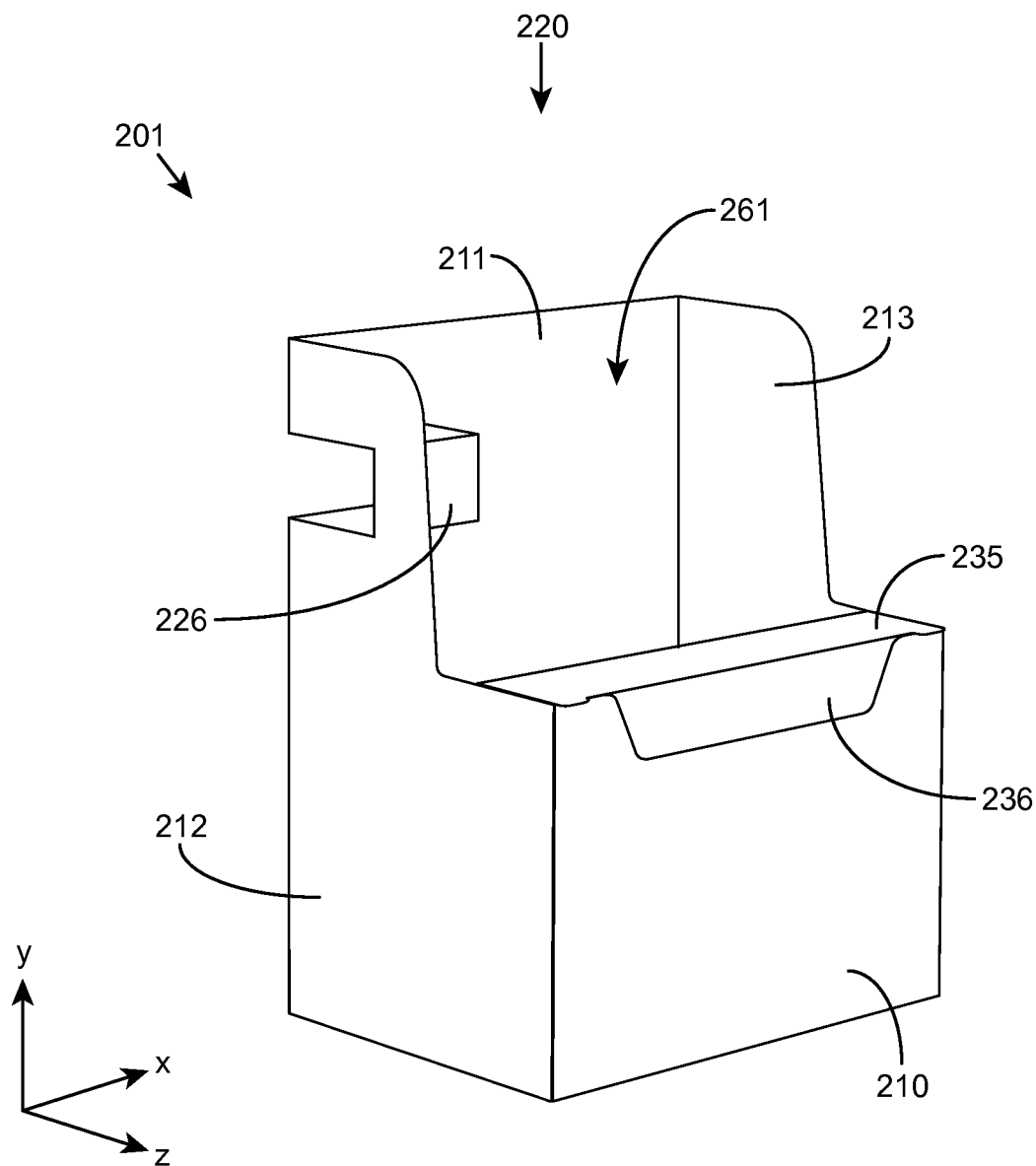
FIG. 3A illustrates a front perspective view of the container of the analyte monitoring device package shown in FIG. 1.
Figure 3B:
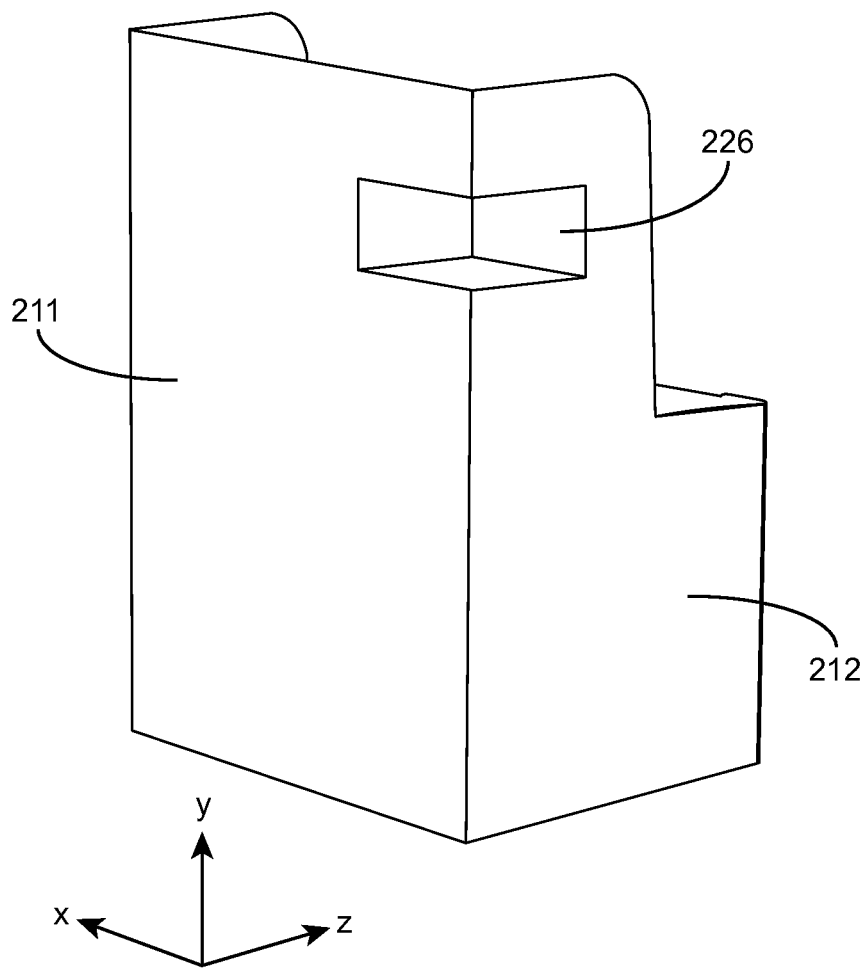
FIG. 3B illustrates a rear perspective view of the container of the analyte monitoring device package shown in FIG. 1.
Figure 4B:
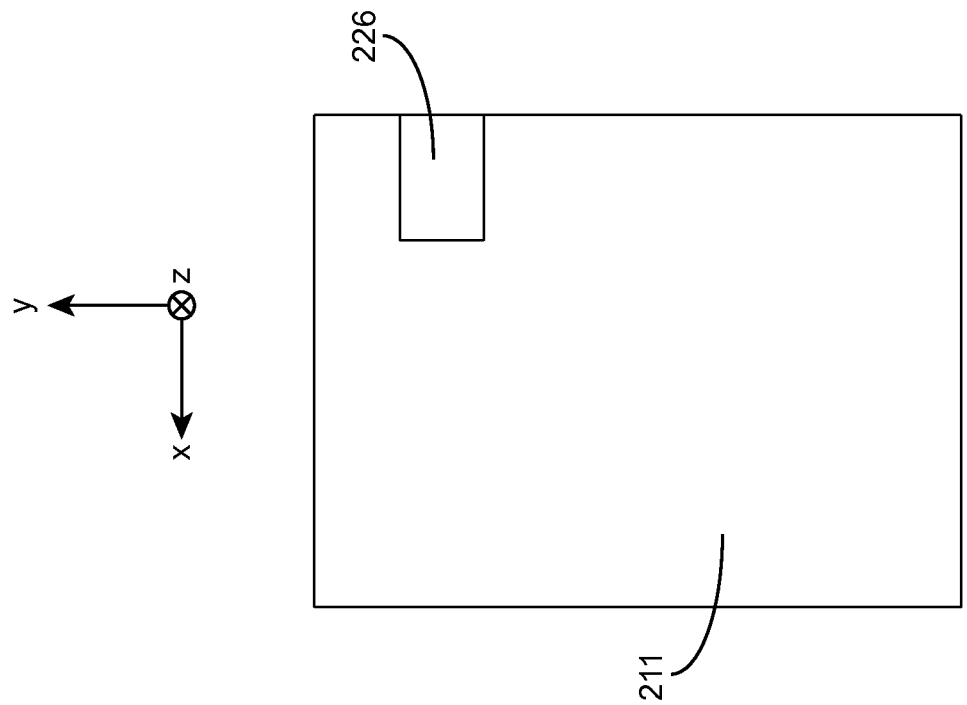
FIGS. 4A, 4B, 4C, 4D, 4E, and 4F illustrate a front view, rear view, right side view, left side view, top view, and bottom view, respectively, of the container shown in FIG. 1.
Figure 4A:
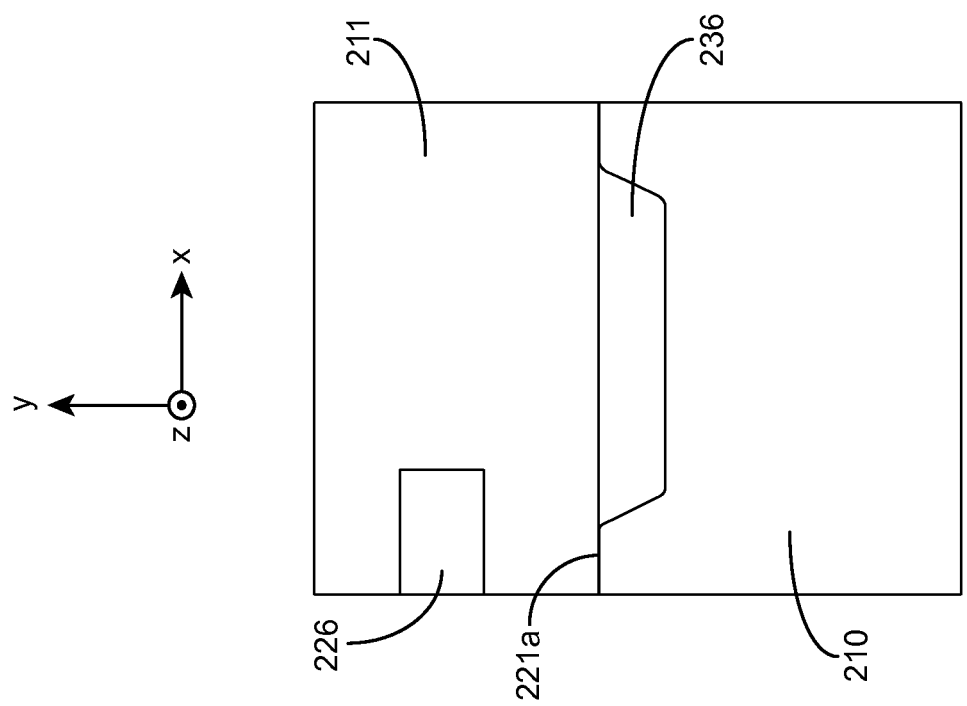
Figure 4D:
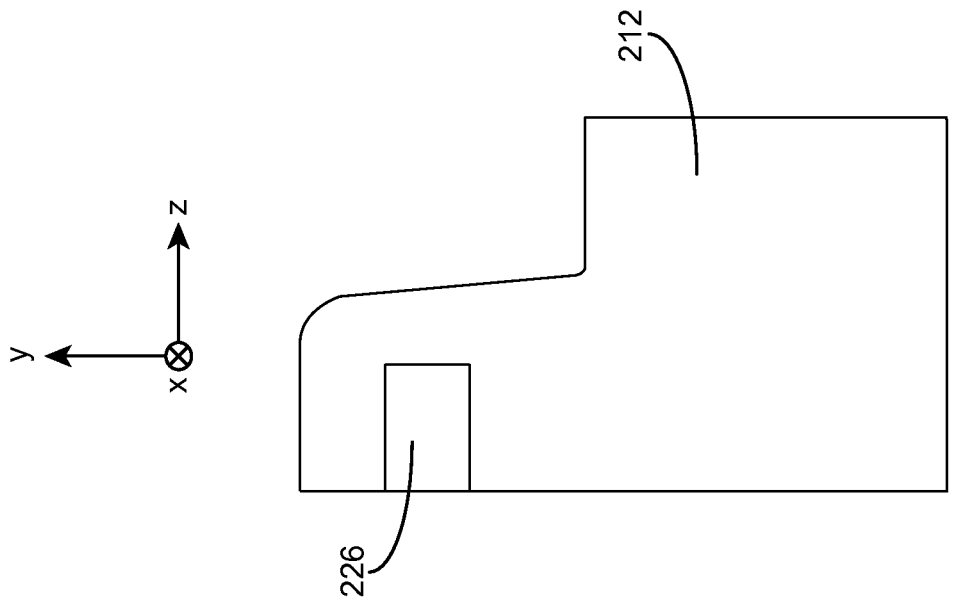
Figure 4C:
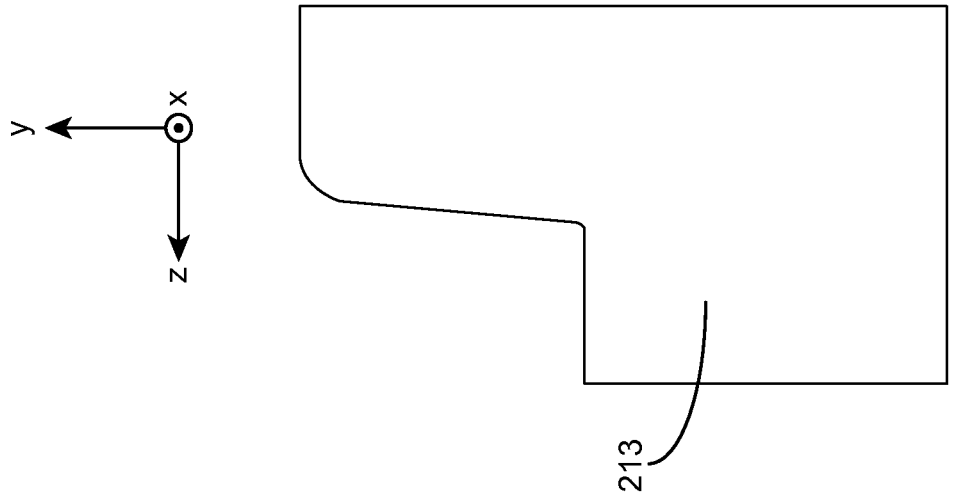
Figure 4F:
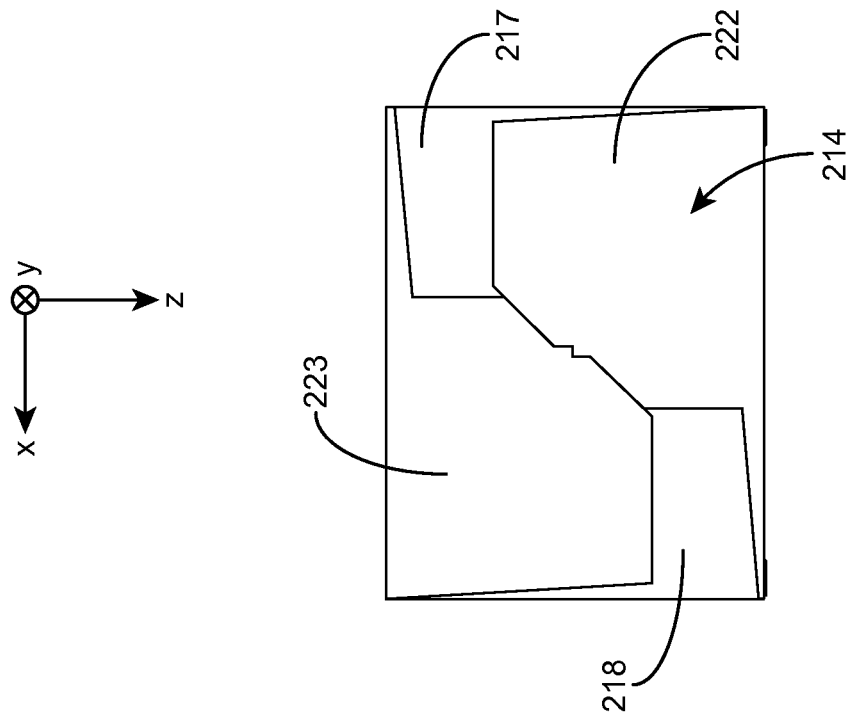
Figure 4E:
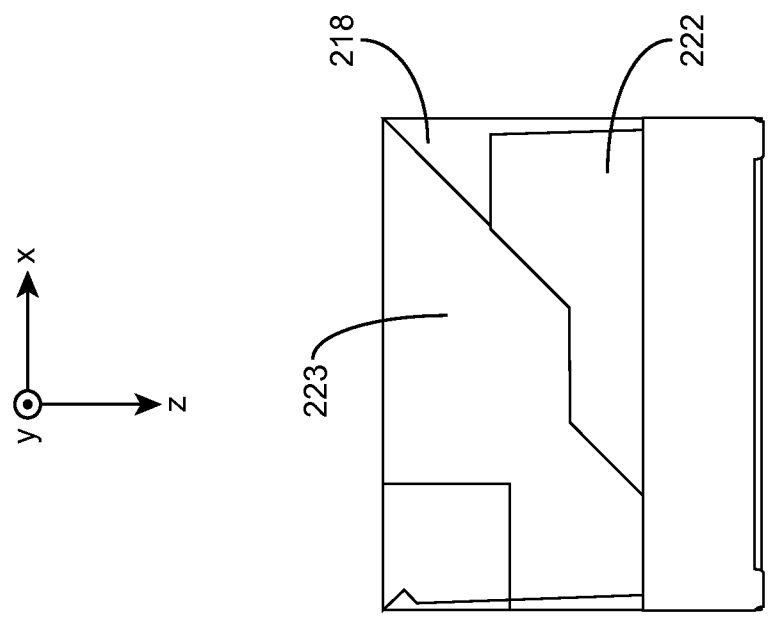
Figure 5:
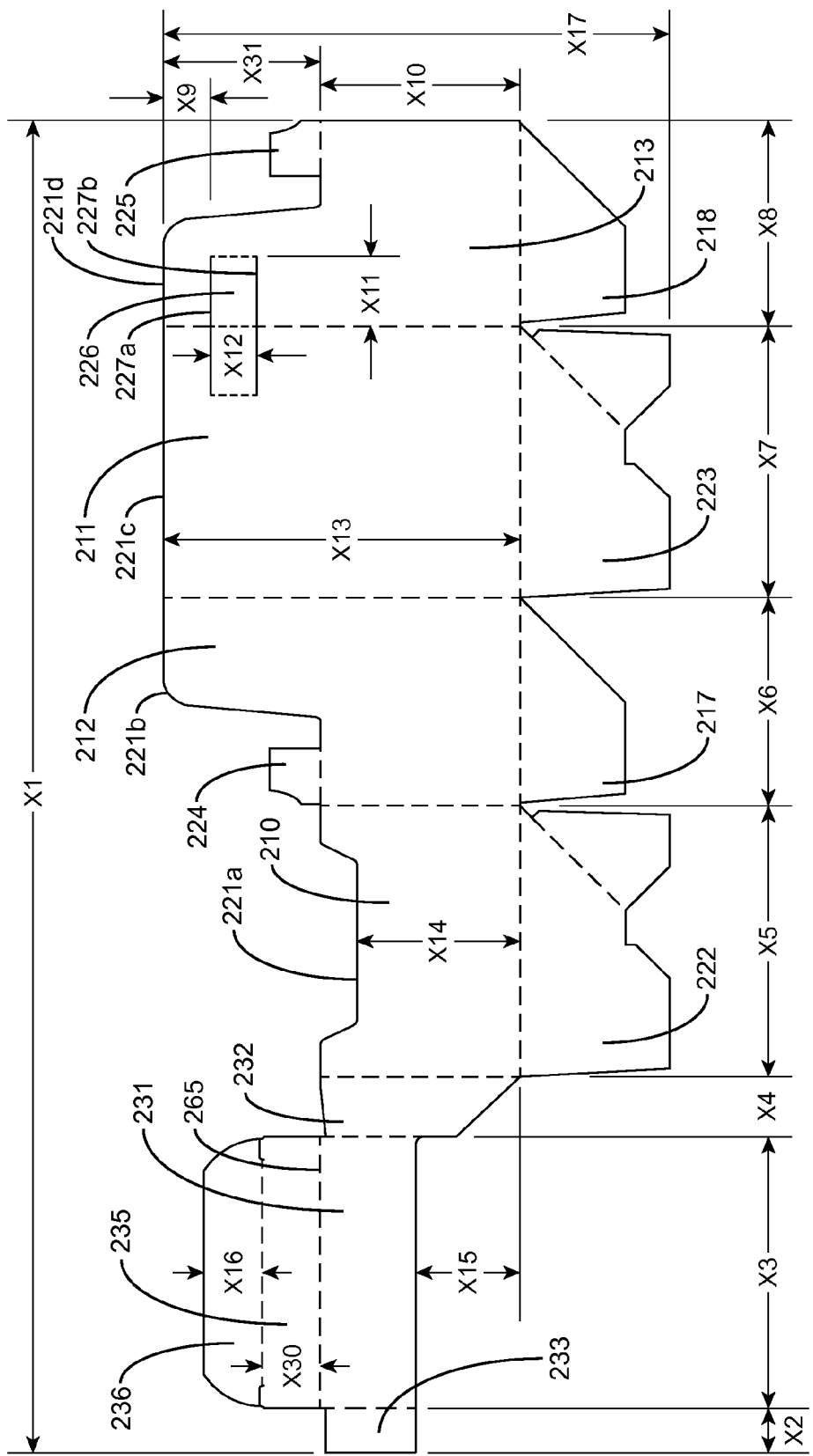
FIG. 5 illustrates a top view of a single sheet of material used to form the container shown in FIG. 1, according to one embodiment.

FIG. 3A illustrates a front perspective view of the container of the analyte monitoring device package shown in FIG. 1. FIG. 3B illustrates a rear perspective view of the container of the analyte monitoring device package shown in FIG. 1. FIGS. 4A, 4B, 4C, 4D, 4E, and 4F illustrate a front view, rear view, right side view, left side view, top view, and bottom view, respectively, of the container of the analyte monitoring device package shown in FIG. 1. FIG. 5 illustrates a top view of a single sheet of material used to form the container of the analyte monitoring device package shown in FIG. 1, according to one embodiment.

Container 201 is formed to be generally rectangular and includes a front wall 210, a rear wall 211, a pair of sidewalls 212 and 213, a bottom wall 214, and an open top end 220. The front wall 210 is shown shorter in height than the rear wall 211. Sidewalls 212 and 213 connect the front wall 210 and rear wall 212. The sidewalls 212 and 213 vary in height from the height of front wall 210 at the side connected to the front wall 210, to the height of the rear wall 211 at the side connected to the rear wall 211. In the example embodiment shown, the walls 210, 211, 212, 213 are integrally formed with, and foldable with respect to its adjacent counterpart.

Front wall 210 includes an upper edge 221*a* and an interengaging member 222 positioned on an opposite side than the upper edge 221*a*. In the example shown, the interengaging member 222 is integrally formed with, and foldable with respect to, the front wall 210.

Rear wall 211 includes an upper edge 221*c* and an interengaging members 223 positioned on an opposite side than the upper edge 221. In the example shown, the interengaging member 223 is integrally formed with, and foldable with respect to, the rear wall 211.

Furthermore, sidewall 212 includes upper edge 221*b* and a retaining flap 217 positioned on an opposite side than the upper edge 221*b*. Similarly, sidewall 213 includes upper edge 221*d* and a retaining flap 218 positioned on an opposite side than the upper edge 221*d*.

Bottom wall 214 is formed from retaining flaps 217 and 218 and interengaging members 222 and 223. The retaining flaps 217 and 218 are integrally formed with, and foldable with respect to, the sidewalls 212 and 213, respectively. The retaining flaps 217 and 218 fold inwardly towards one another when the container 201 is assembled.

The interengaging members 222 and 223 are integrally formed with, and foldable with respect to, the front wall 210 and rear wall 211, respectively. The interengaging members 222 and 223 fold inwardly toward one another and engage each other when the container 201 is assembled.

When the container 201 is assembled, the interengaging members 222 and 223 are folded inwardly toward one another. Different configurations of the retaining flaps 217 and 218 and interengaging members 222 and 223 may be implemented. For example, in one embodiment, the retaining flaps 217 and 218 and interengaging members 222 and 223 are alternated, as shown in FIG. 4F. In another embodiment, the interengaging members 222 and 223 are folded inwardly toward one another on the outside of the retaining flaps 217 and 218 such that the retaining flaps 217 and 218 are positioned within the interior of the container 201.

An interior (shown collectively as compartments 261 and 262 in FIG. 1) of container 201 is formed within front wall 210, rear wall 211, and sidewalls 212 and 213, extending from the bottom wall 214 to upper edges 221a,b,c,d. As will be discussed below, interior of container 201 includes front compartment 262 and rear compartment 261.

It should be appreciated that the upper edges 221a,b,c,d of walls 210,211,212,213 may vary in contour in other embodiments. In the example embodiment shown, upper edge 221a of front wall 210 is curved and recessed in the middle to enable more visibility to the product positioned within the front wall 210. Upper edge 221c of rear wall 211 is shown linear at a fixed height. Upper edges 221b and 221d are shown to have a curved contour that is sloped, providing a varying height from the height of the front wall 210 at the side connected to the front wall 210, to the height of the rear wall 211 at the side connected to the rear wall 211.

Sidewalls 212 and 213 include retaining flaps 224 and 225 on upper edges 221b and 221d, respectively. The retaining flaps 224 and 225 are integrally formed with, and foldable with respect to, sidewalls 212 and 213, respectively. Further, retaining flaps 224 and 225 are positioned on upper edges 221b and 221d, respectively, adjacent to the front wall 210 when assembled.

The container also includes an inner panel 231 that is spaced from the front wall 210 by a spacing panel 232 that enables the inner panel 231 to be positioned interior to, and approximately parallel to, the front wall 210 when assembled. Spacing panel 232 is integrally formed with, and foldable with respect to the front wall 210, and further, integrally formed with, and foldable with respect to, the inner panel 231 on an opposite side of the spacing panel 232.

The inner panel 231 shown includes securing flap 233 integrally formed with, and foldable with respect to, the front wall 210 on a side of the front wall 210 opposite the spacing panel 232.

As shown best in FIG. 5, for assembly, each of the walls 210,211,212,213 are folded inward, for example, to form the generally rectangular shape. The spacing panel 232, inner panel 231, and securing flap 233 are also inwardly folded during assembly and positioned within the interior of the walls 210,211,212,213 of container 201. Securing flap 233 is affixed to the interior side of sidewall 212 by adhesive, for example, to position the inner panel 231 approximately parallel to the front wall 210 within the interior of container 201. Furthermore, the interior side of sidewall 213 may be affixed to the exterior side of spacing panel 232 with adhesive, for example, to secure the inner panel 231 in place.

Inner panel 231 divides the interior of container 201 into a rear compartment 261 between the rear wall 211 and the inner panel 231, and a front compartment 262 between the front wall 210 and inner panel 231. In the embodiment shown, dividing panels 263a,b extend between inner panel 231 and front wall 210 and divide section 262 into three subsections 264a,b,c. Front compartment 262 is represented collectively as subsections 264a,b,c. The columns of space formed by subsections 264a,b,c provide three compartments in which products or product materials may be disposed in. In the embodiment shown, the upper edge 265 of inner panel 231 is aligned with the highest height of upper edge 221a. In this way, the recessed portion of upper edge 221a is below the upper edge 265 of inner panel 231, enabling a good view of products or product materials that may be placed in the subsections 264a,b,c.

Figure 6:
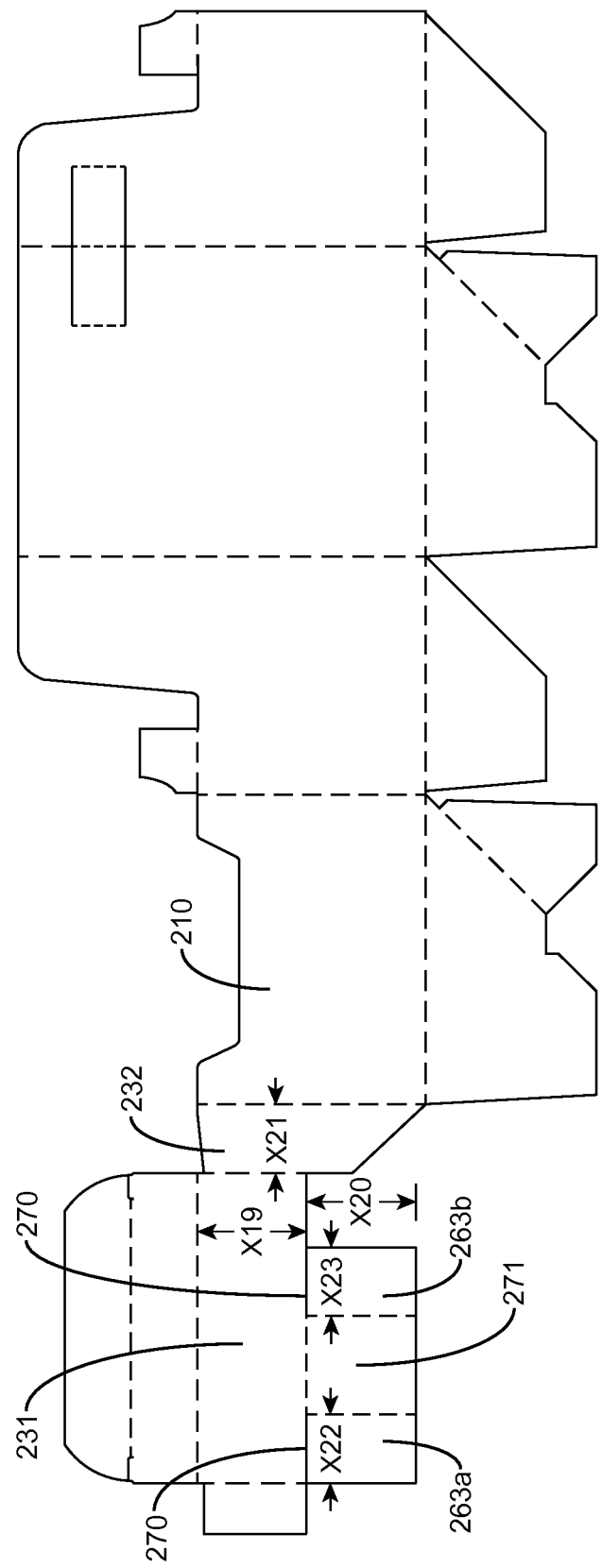
FIG. 6 illustrates a top view of a single sheet of material used to form the container shown in FIG. 1, according to one embodiment.
Figure 7B:
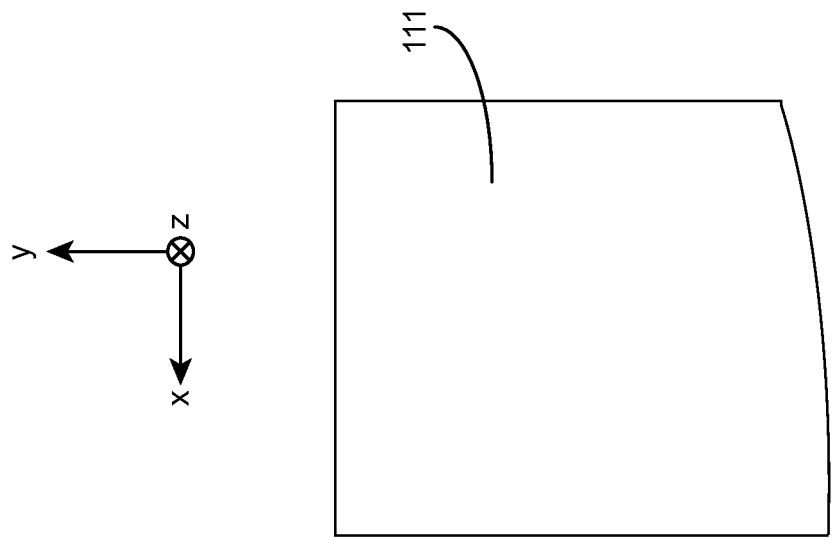
FIGS. 7A, 7B, 7C, 7D, 7E, and 7F illustrate a front view, rear view, right side view, left side view, top view, and bottom view, respectively, of the cover shown in FIG. 1.
Figure 7A:
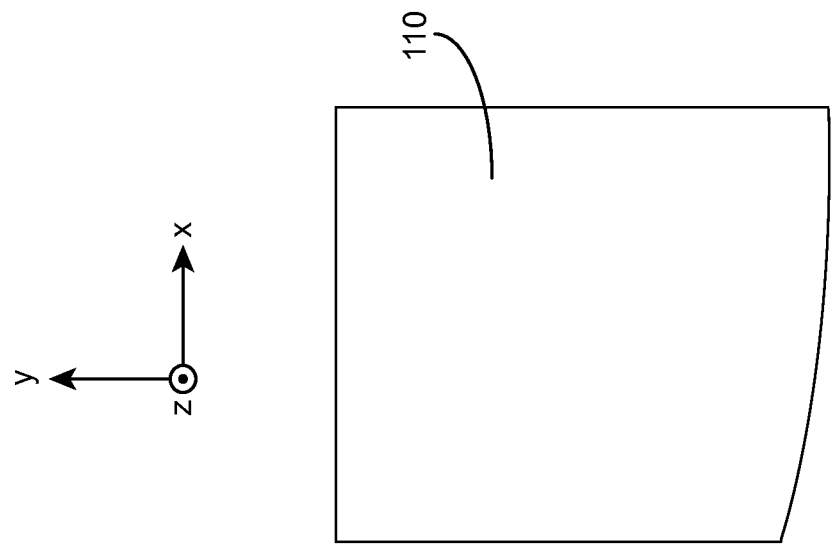
Figure 7D:
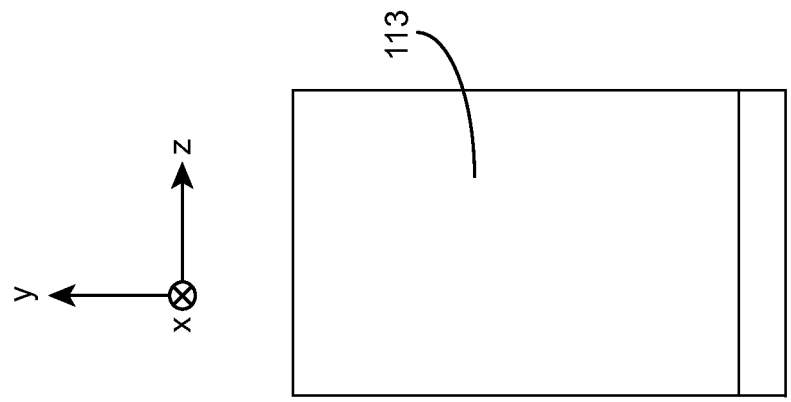
Figure 7C:
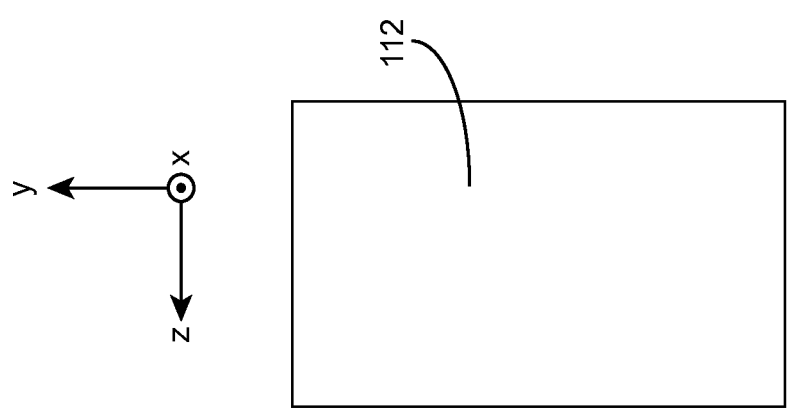
Figure 7F:
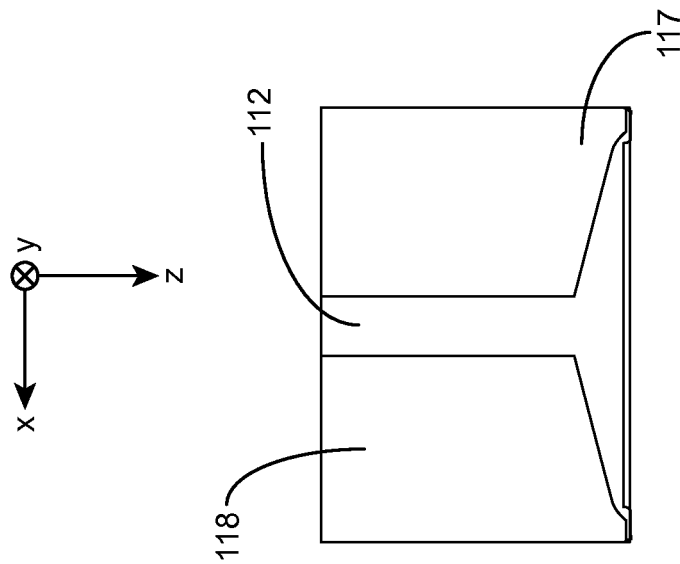
Figure 7E:
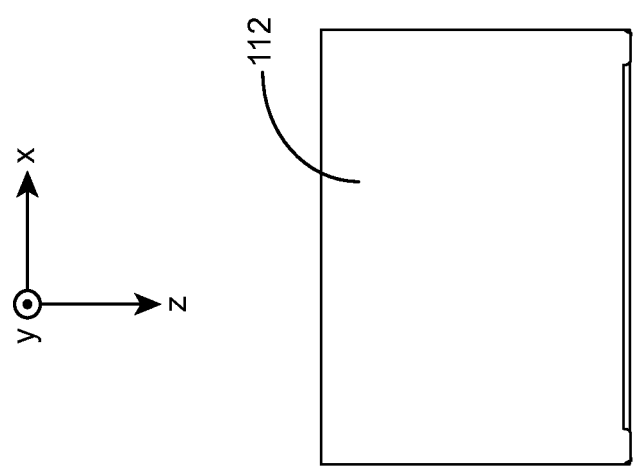

In one embodiment, the dividing panels 263a,b are inserted within section 262, or attached to the inner panel 231, and not formed from the unitary piece of material of the rest of container 201. In another embodiment, dividing panels 263a,b,c are formed as part of a unitary piece of material along with the rest of container 201. FIG. 6 illustrates a top-side view of a single sheet of material used to form the container of the analyte monitoring device package shown in FIG. 1, according to one embodiment. For the sake of clarity and brevity, a number of common features of FIG. 5 and FIG. 6 are not represented in FIG. 6 or described in great detail again.

In the embodiment shown in FIG. 6, inner panel 231 is connected to spacing panel 232 which is connected to front wall 210. Inner panel 231 is also integrally formed with, and foldable with respect to base flap 271. Base flap 271 is integrally formed with, and foldable with respect to dividing panels 263a,b. The dotted lines illustrate the fold lines in which the sheet of material is folded for assembly. The dividing panels 263a and 263b are on opposite sides of the base flap 271. Dividing panels 263 are separated from inner panel 231 along cut lines 270. In this way, when base flap 271 is bent inward and against inner panel 231, cut lines 270 enable dividing panels 270 to bend at 90 degrees from the base flap 271 to form subsections 264a,b,c. The base flap 271 may be bent against inner panel, or alternatively affixed, or otherwise, attached to inner panel 231, such as with adhesive. In order for dividing panels 270 to extend from inner panel 231 to front wall 210, the widths X22 and X23 of dividing panels 263a and 263b, respectively, should approximate the width X21 of spacing panel 232. Furthermore, for the dividing panels 263a,b to extend the length X19 of the inner panel 231, the lengths X20 of the dividing panels 263a,b should be approximately equal to the length X19 of the inner panel 231.

It should be appreciated that a different number of dividing panels may be implemented in other embodiments. For example, one dividing panel, three dividing panels, etc., may be implemented to provide a different number of subsections in front compartment 262. It should also be appreciated that the dividing panels may be constructed in a different manner in other embodiments.

In the embodiments shown, the inner panel 231 does not extend all the way down to the bottom wall 214. In this way, compartments 261 and 262 are connected near the bottom wall 214, but inner panel 231 still provides support for taller items. In another embodiment, inner panel 231 extends all the way down to the bottom wall 214 to provide compartments 261 and 262 that are isolated from each other. It should also be appreciated that the dividing panels 263a,b may also be various lengths in other embodiments—e.g., extending partially or completely to the bottom wall 214.

The inner panel 231 also includes a cover flap 235 that is integrally formed with, and foldable with respect to, the inner panel 231. Opposite the foldable connection with the inner panel 231, cover flap 235 includes engagement tab 236 that is integrally formed with, and foldable with respect to the cover flap 235 such that the engagement tab 236 may extend perpendicular to the cover flap 235 when assembled. In this way, the tab 236 can be engaged between the front wall 210 and retaining flaps 224 and 225 to hold the cover flap 235 in a closed position over the front compartment 262 when assembled. When the cover flap 235 is closed, retaining flaps 224 and 225 are folded inwardly toward one another with the cover flap 235 folding over the outside of retaining flaps 224 and 225.

In one embodiment, the container includes a retention element along one or more walls of the container. The retention element serves to retain a product or product material, such as a test strip vial for example.

In the embodiment shown, container 201 includes a retention element 226 that is formed as an inverse cutout in the rear wall 211 and sidewall 213. Cut lines 227a,b are made within rear wall 211 and sidewall 213 and the retention element 226 is integrally formed with, and foldable with respect to each of the rear wall 211 and sidewall 213. The retention element 226 is then bent inward within rear compartment 261 to form a retaining mechanism to retain a product or product material between the retention element 226, rear wall 211 and sidewall 213. For example, a test strip vial may be inserted within the space between the retention element 226, rear wall 211 and sidewall 213 such that the cap of the strip vial contacts the retention element 226 to maintain the strip vial in place.

In the embodiments shown, the container 201 is formed from one unitary piece of material that is folded to form the assembled container 201. It should be appreciated that in other embodiments, various portions of the container 201 (e.g., walls 210,211,212,213, inner panel 231, cover flap 235, retaining flaps 217,218,224,225, securing members 233, retention element 226, etc., may be initially formed as separate members that are subsequently secured, or otherwise affixed, to one another in any suitable manner to form the desired configuration for the container 201. Further, the particular configuration and/or shape of the various portions of container 201 may be varied as necessary to be other than rectangular, and the number may be varied as necessary to form a container having the desired shape or cross-section, which can be other than rectangular or square, e.g., polygonal, circular, etc. Also, it is contemplated that any suitable material (or materials) can be utilized to form the container 201, such as conventional paperboard, cardboard material, transparent material (e.g., clear acetate), polymeric material such as plastic, etc., or any combination thereof.

It should be appreciated that the actual dimensions represented by the reference numerals beginning with the letter "X" may vary in size in different embodiments. For example, in one example embodiment, some of the dimensions of the container (shown in inches) are as follows:

| | |
|---|---|
| X1 | 22 3/8 |
| X2 | 3/4 |
| X3 | 4 17/32 |
| X4 | 1 |
| X5 | 4 9/16 |
| X6 | 3 1/2 |
| X7 | 4 9/16 |
| X8 | 3 15/32 |
| X9 | 13/16 |
| X10 | 3 3/8 |

-continued

| | |
|---|---|
| X11 | 1 5/32 |
| X12 | 3/4 |
| X13 | 6 |
| X14 | 2 3/4 |
| X15 | 1 3/4 |
| X16 | 1 |
| X17 | 8 1/2 |

It should be appreciated that the preceding example dimensions provided are exemplary and are not intended to be limiting.

Figure 8:
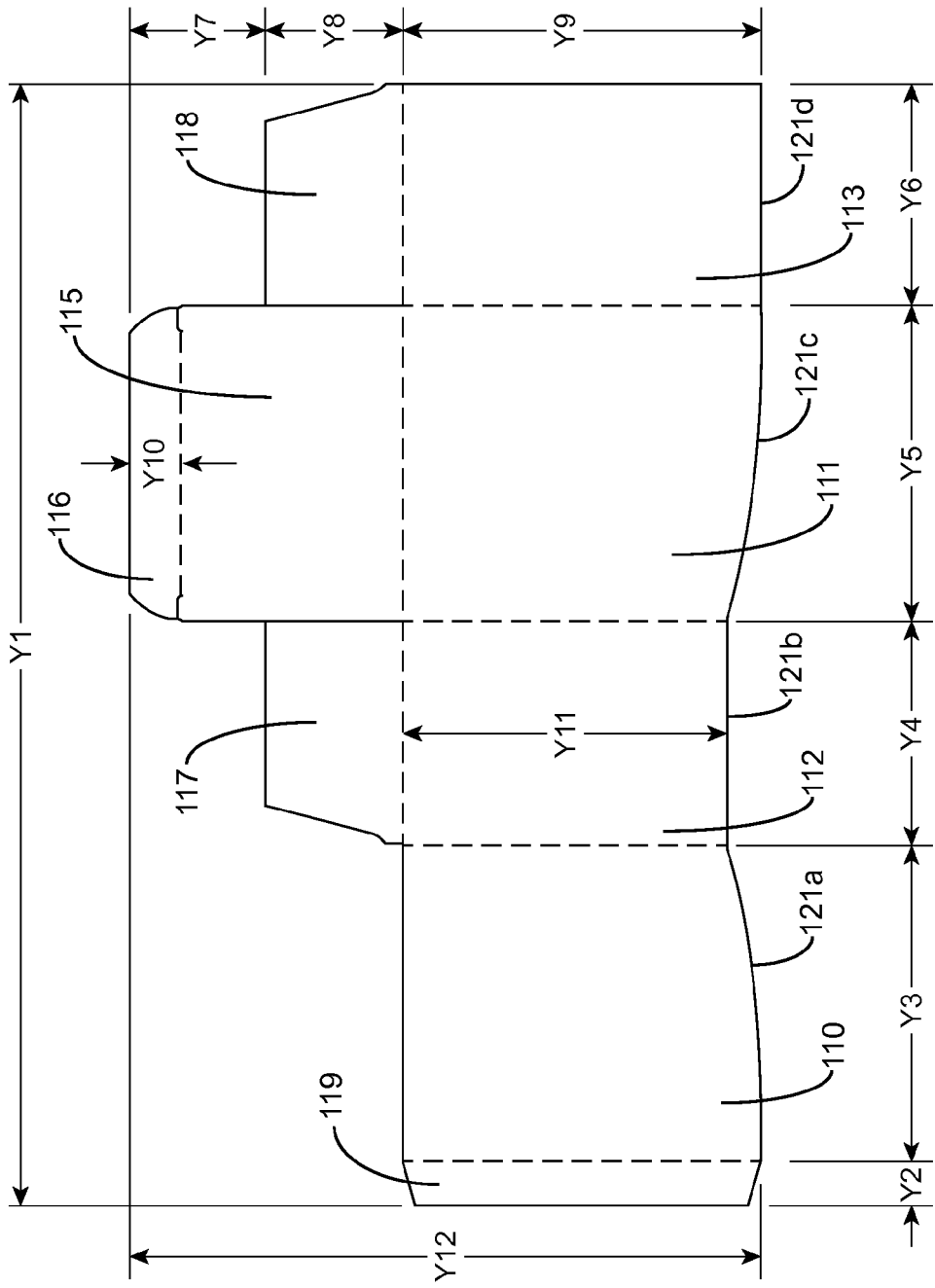
FIG. 8 illustrates a top view of a single sheet of material used to form the cover shown in FIG. 1, according to one embodiment.

In the embodiment shown in FIG. 1, the package includes cover 201. FIGS. 7A, 7B, 7C, 7D, 7E, and 7F illustrate a front view, rear view, right side view, left side view, top view, and bottom view, respectively, of the cover of the analyte monitoring device package shown in FIG. 1. FIG. 8 illustrates a top view of a single sheet of material used to form the cover of the analyte monitoring device package shown in FIG. 1, according to one embodiment.

Cover 101 is formed to be generally rectangular, including a front wall 110, a rear wall 111, a left sidewall 112, a right sidewall 113, and a top wall 114. Walls 110,111,112,113 are integrally formed with, and foldable with respect to its adjacent counterpart. Securing flap 119 is shown integrally formed with, and foldable with respect to, the front wall 110 opposite sidewall 112. Each of the walls 110,111,112,113 are folded inward and securing flap 119 affixes to sidewall 113 with adhesive, for example, to form a generally rectangular shape.

In the example embodiment shown, each of the respective walls forming the cover 101 are integrally formed with one another from a unitary piece of a material suitable for forming a packaging cover. In other embodiments, the cover may be formed of two or more pieces that are adhered to one another, or otherwise affixed to one another.

Top wall 114 is formed from cover flap 115 and retaining flaps 117 and 118. The retaining flaps 117 and 118 are integrally formed with, and foldable with respect to, the sidewalls 112 and 113, respectively. The cover flap 115 is integrally formed with, and foldable with respect to, the rear wall 111. Opposite the foldable connection with the rear wall 111, cover flap 115 includes engagement tab 116 that is formed with, and foldable with respect to the cover flap 115 such that the engagement tab 116 may extend perpendicular to the cover flap 115. In this way, the tab 116 can be engaged between the front wall 110 and retaining flaps 117 and 118 to hold the cover flap 115 in a closed position over the interior of the cover 101 when assembled.

It should be appreciated that in other embodiments, the cover flap 115 and retaining flaps 117 and 118 may be integrally formed with, and foldable with respect to, any of the walls 110,111,112,113.

Bottom edges 121a,b,c,d of walls 110,112,111,113, respectively, define an open bottom end 120 opposite the top wall 114. The open bottom end 120 is shaped and sized to permit the top end 220 of container 201 to be received within the interior of the cover 101. It should be appreciated that the bottom edges 121a,b,c,d of walls 110,111,112,113 may vary in contour. For example, as shown in the example embodiment, edges 121a and 121c are shown to have a curved contour while edges 121b and 121d have a linear contour. The curved contour may serve to identify the proper orientation of the package and facilitate the removing of the cover from the container. The user may be able to more easily grip the bottom edges 121a and 121c of the cover 101 when the package 100 is resting on a countertop. In some instances, the cover may be secured to the container with a securing element such as adhesive, tape, security seals, ribbon, etc.

To cover the container 201, the cover 101 is placed over the container 201—e.g., by moving the cover 101 downward in the negative y-direction to receive the top end 220 of the container 201. When the cover 101 is placed completely over the container 201, the inside of top wall 114 contacts the top edges 221b,c,d of container 201.

It should be appreciated that in other embodiments, walls 110,111,112,113, cover flap 115, securing flap 119, and retaining flaps 117 and 118 may be initially formed as separate members that are subsequently secured, or otherwise affixed, to one another in any suitable manner to form the desired configuration for the cover 101. Further, the particular configuration and/or shape of the walls 110,111,112,113, cover flap 115, securing flap 119, and retaining flaps 117 and 118 may be varied as necessary to be other than rectangular, and the number of sidewalls 112 and 113, cover flap 115, securing flap 119, and retaining flaps 117 and 118 may be varied as necessary to form a cover 101 having the desired shape or cross-section, which can be other than rectangular or square, e.g., polygonal, circular, etc.

Also, it is contemplated that any suitable material (or materials) can be utilized to form the cover 101, such as conventional paperboard, cardboard material, transparent material (e.g., clear acetate), polymeric material such as plastic, etc., or any combination thereof. Transparent material may be used, for example, to permit some or all of the products within the cover 101 to be seen through the cover 101.

It should be appreciated that the actual dimensions represented by the reference numerals beginning with the letter "Y" may vary in size in different embodiments. For example, in one example embodiment, some of the dimensions of the cover (shown in inches) are as follows:

| | |
|---|---|
| Y1 | 16 9/16 |
| Y2 | 21/32 |
| Y3 | 4 21/32 |
| Y4 | 3 5/16 |
| Y5 | 4 21/32 |
| Y6 | 3 9/32 |
| Y7 | 2 1/64 |
| Y8 | 2 1/64 |
| Y9 | 5 9/32 |
| Y10 | 3/4 |
| Y11 | 4 25/32 |
| Y12 | 9 5/16 |

It should be appreciated that the preceding example dimensions provided are exemplary and are not intended to be limiting.

Referring back to container 201, in some aspects of the present disclosure, cover flap 235 may also serve as a base surface for one or more additional products or product materials to be placed. Because of the configuration of the container 201 (e.g., position and orientation of the cover flap 235 when closed, the shape of the sidewalls 212,213, etc.), products or product materials may be disposed on the cover flap 235 and be contained within the space above the cover flap 235 and inside of cover 101. The one or more additional products or product materials may be disposed in the package to form an analyte monitoring kit, for example. In some instances, taller product material such as manuals, instruction booklets, product specification manuals, marketing brochures, etc., may be placed within rear compartment 261, and other products or materials (e.g., analyte test strip box) may be disposed on the cover flap 235 serving as a base, with the taller product materials providing additional support and stabilization for the product or materials disposed on the cover flap 235.

In some aspects of the present disclosure, the package includes an ancillary container 301 that is disposed on the cover flap 235 of container 201 and contained within the space between the cover flap 235 and top wall 114 of the cover 101 when the cover 101 is on the container 201. The ancillary container may contain any variety of analyte related products or product materials. In one embodiment, the ancillary container is a box of analyte test strips (e.g., glucose test strips). For example, the analyte test strips may be of any kind, size, or shape known to those skilled in the art; for example, FREESTYLE® and FREESTYLE LITE™ test strips, as well as PRECISION™ test strips sold by ABBOTT DIABETES CARE Inc. The analyte monitoring devices of the present disclosure may be configured to work with a wide variety of analyte test strips, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. No. 6,616,819; U.S. Pat. No. 6,143,164; U.S. Pat. No. 6,592,745; U.S. Pat. No. 6,071,391 and U.S. Pat. No. 6,893,545; the disclosures of each of which are incorporated by reference herein in their entirety.

Figure 9:
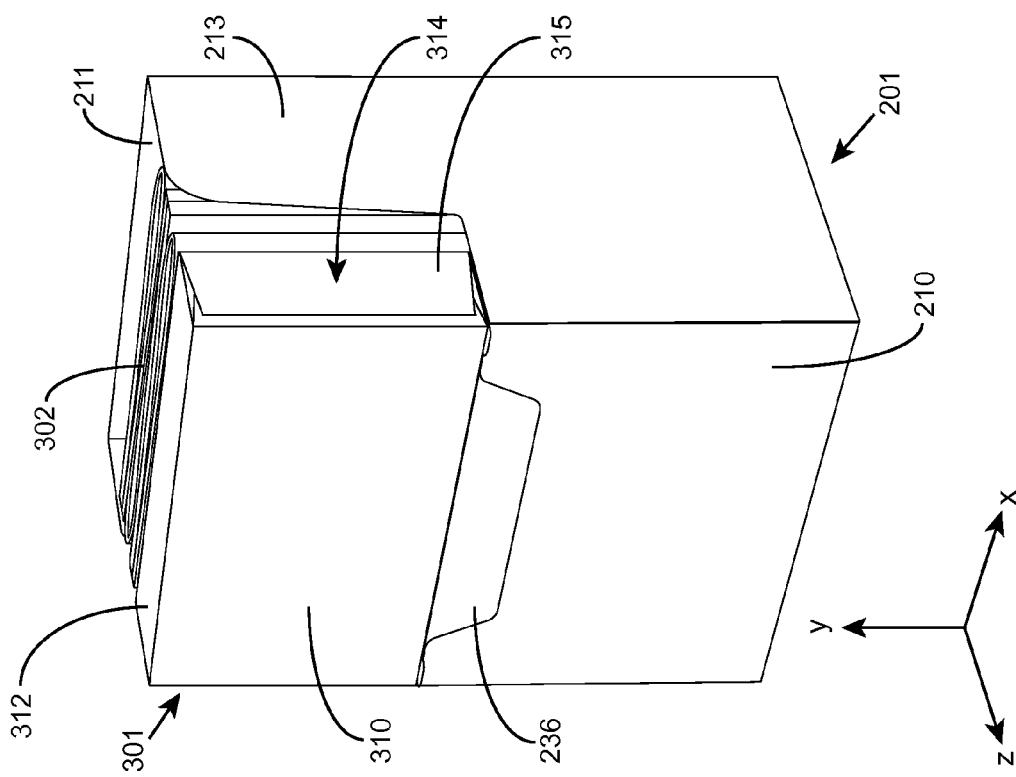
FIG. 9 illustrates a front perspective view of an ancillary container disposed on the container shown in FIG. 1, according to one embodiment.

FIG. 9 illustrates an ancillary container disposed on the container in FIG. 1, according to one embodiment. The ancillary container 301 is shown disposed on cover flap 235 of container 201. A package of the present disclosure may also include a cover 101 that is disposed over the container 201 and ancillary container 301. In such case, the ancillary container 301 is disposed on top of the cover flap 235 within the interior space between the cover flap 235 and top wall 114 of the cover 101.

It should be appreciated that in some embodiments, the package includes the ancillary container—e.g., container 201, cover 101, and ancillary container 301. In other embodiments, an analyte monitoring kit includes a package (e.g., container 201 and cover 101) along with product or product materials, such as an ancillary container (e.g., glucose test strips).

In one embodiment, the ancillary container 301 is shaped and sized to fit on the cover flap 235 of the front compartment 262 between the cover flap 235 and the top wall 114 of the cover 101, wherein a length and width of a contacting side of the ancillary container 301 matches a length and width of the cover flap that the contacting side is disposed on. The ancillary container 301 shown is sized and shaped to approximately align with the front wall 210 of container 201 and with the top edge 221c of the rear wall 211, thus approximating the dimensions of the cover 101 that fits over it.

Figure 10:
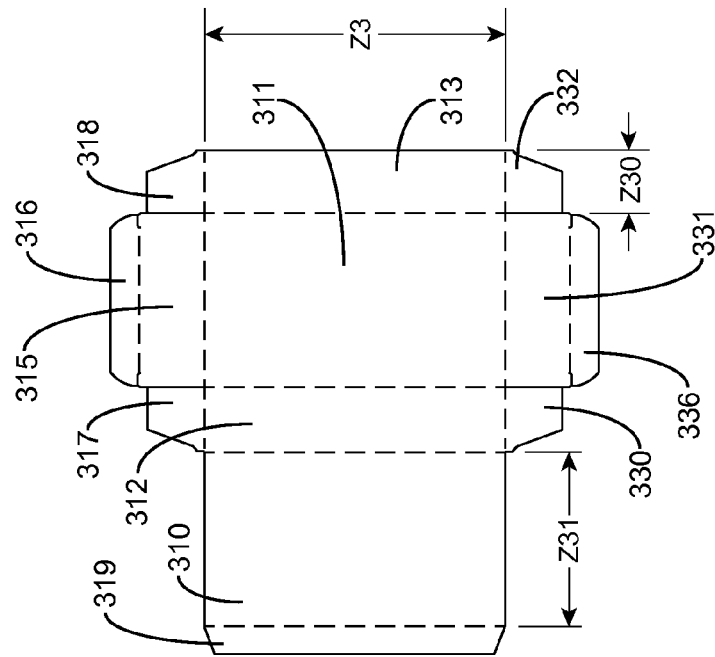
FIG. 10 illustrates a top view of a single sheet of material used to form an ancillary container, according to one embodiment.

FIG. 10 illustrates a sheet of material used to form an ancillary container, according to one embodiment. The ancillary container 301 is formed to be generally rectangular when assembled, including a front wall 310, a rear wall 311 opposite the front wall 310, a top sidewall 312, a bottom sidewall 313 opposite the top sidewall 312, end wall 314, and end wall 334 opposite end wall 314.

In the example embodiment shown, the walls 310,311,312, 313 are integrally formed with, and foldable with respect to its adjacent counterpart. Securing flap 319 is shown integrally formed with, and foldable with respect to, the front wall 310. Each of the walls 310,311,312,313 are folded inward and securing flap 319 is affixed to sidewall 313 with adhesive, for example, to form the generally rectangular shape.

In the example embodiment shown, each of the respective walls forming the ancillary container 301 are integrally formed with one another from a unitary piece of a material suitable for forming the ancillary container. In other embodiments, the ancillary container may be formed of two or more pieces that are adhered to one another, or otherwise affixed to one another.

End wall 314 is formed generally from cover flap 315 and retaining flaps 317 and 318. The retaining flaps 317 and 318 are integrally formed with, and foldable with respect to, the top sidewall 312 and bottom sidewall 313, respectively. The cover flap 315 is integrally formed with, and foldable with respect to, the rear wall 311. Opposite the foldable connection with the rear wall 311, cover flap 315 includes engagement tab 316 that is formed with, and foldable with respect to the cover flap 315 such that the engagement tab 316 may extend perpendicular to the cover flap 315. In this way, the tab 316 can be engaged between the front wall 310 and retaining flaps 317 and 318 to hold the cover flap 315 in a closed position over the interior of the ancillary container 301 when assembled.

Similarly, end wall 334 is formed generally from cover flap 331 and retaining flaps 330 and 332. The retaining flaps 330 and 332 are integrally formed with, and foldable with respect to, the top sidewall 312 and bottom sidewall 313, respectively. The cover flap 331 is integrally formed with, and foldable with respect to, the rear wall 311. Opposite the foldable connection with the rear wall 311, cover flap 331 includes engagement tab 336 that is formed with, and foldable with respect to the cover flap 331 such that the engagement tab 336 may extend perpendicular to the cover flap 331. In this way, the tab 336 can be engaged between the front wall 310 and retaining flaps 320 and 322 to hold the cover flap 331 in a closed position over the interior of the ancillary container 301 when assembled.

It should be appreciated that in other embodiments, the cover flaps 315,331 and retaining flaps 317,318,330,332 may be integrally formed with, and foldable with respect to, any of the walls 310,311,312,313. Further, it should be appreciated that other configurations for end wall 314 and end wall 334 may be implemented, such as shown in FIG. 9.

Top sidewall 312 and bottom sidewall 313 are on opposite sides of ancillary container 301 and extend from the front wall 310 and rear wall 311 when assembled. In the embodiment where the ancillary container 301 is shaped and sized to fit on the cover flap 235 of the front compartment 262 between the cover flap 235 and the top wall 114 of the cover 101, wherein a length and width of a contacting side of the ancillary container matches a length and width of the cover flap that the contacting side is disposed on, the width Z30 of the bottom sidewall 313 approximates the width X30 of the cover flap 235 of container 201. Similarly, the length Z3 of bottom sidewall 313 approximates the length X3 of the cover flap 235 of container 201. As top sidewall 312 and bottom sidewall 313 are similarly shaped and sized in the embodiment shown, the top sidewall 312 has equal dimensions to the bottom sidewall 313.

Furthermore, in some instances, the width Z31 of the front wall 310 approximates the length X31 of container 301. Length X31 represents the distance between the height of the cover flap 235 to the top edge (e.g., edge 221c) of the container 301. In this way, the container 201 and ancillary container 301 form a generally rectangular shape that form fits with the cover 101. In other embodiments, the width Z31 of front wall 310 is less than length X31 of container 301.

It should be appreciated that in other embodiments, walls 310,311,312,313, securing flap 119, cover flaps 315,331, and retaining flaps 317,318,330,332 may be initially formed as separate members that are subsequently secured, or otherwise affixed, to one another in any suitable manner to form the desired configuration for the ancillary container 301. Further, the particular configuration and/or shape of the walls 310, 311,312,313, securing flap 319, cover flaps 315,331, and retaining flaps 317,318,330,332 may be varied as necessary to be other than rectangular, and the number of walls 310,311, 312,313, securing flap 319, cover flaps 315,331 and retaining flaps 317,318,330,332 may be varied as necessary to form an ancillary container having the desired shape or cross-section, which can be other than rectangular or square, e.g., polygonal, circular, etc.

Also, it is contemplated that any suitable material (or materials) can be utilized to form the ancillary container 301, such as conventional paperboard, cardboard material, transparent material (e.g., clear acetate), etc., or any combination thereof. Transparent material may be used, for example, to permit some or all of the products within the ancillary container 301 to be seen through the ancillary container 301.

In the embodiment shown, the container 201 is shown having product materials 302 (e.g., literature related to the analyte monitoring device) disposed in the rear compartment 261—e.g., as may be provided within a kit including the container 201 and ancillary container 301. The product materials 302 may also serve to provide support and help stabilize the ancillary container 301.

In some aspects of the present disclosure, an analyte monitoring kit is provided. The analyte monitoring kit includes a package for an analyte monitoring device, such as described above, as well as an analyte monitoring device disposed therein. For example, the package includes a container for containing an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container. The kit also includes an analyte monitoring device disposed in the container.

In some aspects of the present disclosure, an analyte monitoring kit is provided. The analyte monitoring kit includes an analyte monitoring device package as well as one or more products and/or product materials.

Figure 11:
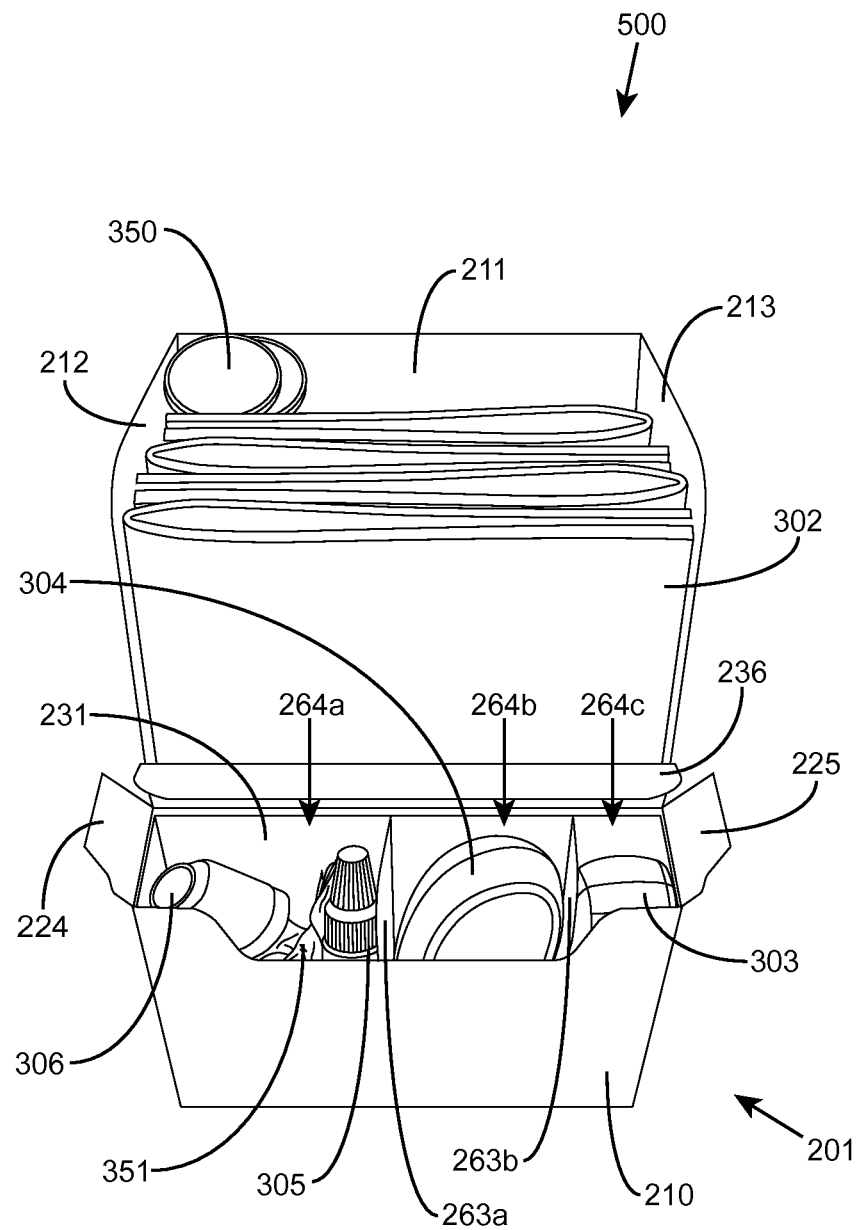
FIG. 11 illustrates a top perspective view of an analyte monitoring kit, according to one embodiment.

FIG. 11 illustrates a top perspective view of an analyte monitoring kit, according to one embodiment. Analyte monitoring kit 500 includes container 201, such as shown in the previous figures, with analyte monitoring device 304. The analyte monitoring device 304 is disposed in subsection 264b of the front compartment 262 of the container 201. The container 201 also includes a control solution 305, an alternate site testing (AST) cap 306, and lancets 351 disposed in subsection 264a of the front compartment 262 of the container 201. The container 201 also includes a lancing device 303 disposed in subsection 264c of the front compartment 262 of container 201. The analyte monitoring kit shown also includes literature 302 related to the analyte monitoring device disposed in the rear compartment 261 of the container 201. Example literature may include, but is not limited to, one or more of the following: product manuals, warranty cards, logbooks, flyers. Also disposed in the rear compartment 261 is a strip vial 350, which is disposed between the retention element 226 and side 212 and rear wall 211. The rear compartment 261 may also contain a carrying case for one or more products, such as analyte monitoring device, medication delivery device, lancing device, etc. In other embodiments, the kit may also include a medication delivery device (e.g., insulin delivery device) disposed within the rear compartment 261 or front compartment 260.

As shown in the example embodiment shown, the front compartment 262 and rear compartment 261 are easily viewed when in front of the container 201. This enables a patient or user to easily see most or all products and product materials in the container and to easily tell where products and product materials are located. Furthermore, it provides a user friendly organization which enables the patients or users to become familiar with. Moreover, with the upper edge of the front wall being recessed, an even better view within the front compartment is provided.

It should be appreciated that the cover 101, while not shown in FIG. 11, is placed on top of the top end 220 of container 201 when all the products and product materials are disposed in the container 201. In one embodiment, the analyte is glucose and the analyte monitoring device is a glucose monitoring device (e.g., glucose meter).

It should be appreciated that in other embodiments, one or more of the products and product materials may be disposed in a different subsection and/or compartment of the container 201. For example, in one embodiment, the container may include an analyte monitoring device (e.g., glucose meter) disposed in subsection 264a; lancets and AST cap disposed in subsection 264b; and a lancing device disposed the rear compartment 261. Furthermore, it should be appreciated that in other embodiments, not all products and product materials shown may be included in a kit. Further, in other embodiments, additional products or product materials not shown may be included in the kit.

In some aspects of the present disclosure, a method of making a package for an analyte monitoring device is provided. The method includes providing a sheet of material, and generating a first cutout from the sheet of material. The shape of the first cutout is such that when folded in a plurality of locations, a container is formed. The method also includes folding the first cutout in a plurality of location to form a container for an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container.

Figure 12:
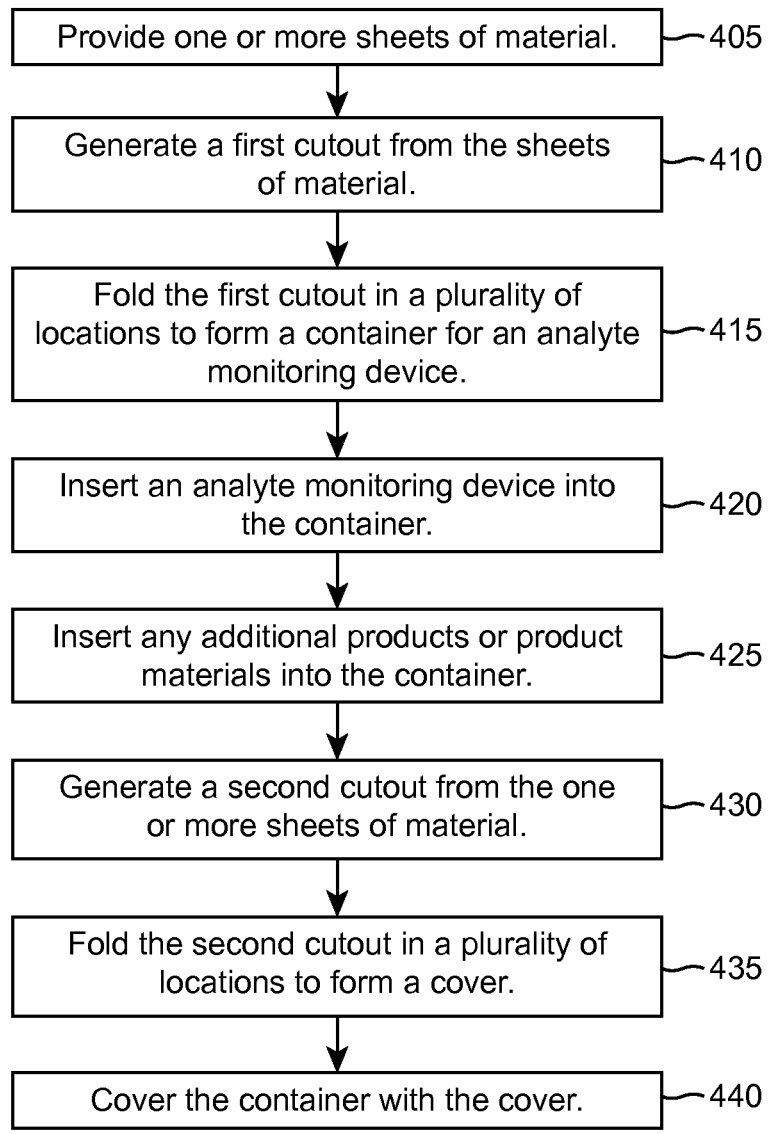
FIG. 12 illustrates a flowchart for making a package for an analyte monitoring device, according to one embodiment.

FIG. 12 illustrates a flowchart for making a package for an analyte monitoring device, according to one embodiment. At block 405, one or more sheets of material are provided. A cutout is made from one of the sheets of material, as represented by block 410. The cutout is shaped and sized for forming a container—e.g., such as shown in FIGS. 5 and 6. The cutout may be generated in any variety of manners to separate the cutout from the sheet of material. For example, the cutting of the cutout may include cutting, tearing, stamping, etc., with a blade, scissors, stamping machine, etc. The generating of the cutouts includes forming the cut lines for the retention element. In other embodiments, the cut lines for the retention elements may be formed before or after the cutout is generated.

Once the cutout is formed, the cutout is folded to form the container for the analyte monitoring device, as represented by block 415. The cutout may be folded manually by persons or machine. Once the container is formed, the analyte monitoring device is inserted into the container, as represented by block 420. In one embodiment, the analyte monitoring device is inserted in the front compartment. At block 425, any additional products or product materials are inserted into the container, either in the front compartment or rear compartment. Example products or product materials which may be additionally inserted into the container may include, but are not limited to, one or more of the following: lancing device; lancets; control solution; carrying case; and literature related to the analyte monitoring device, such as product manuals, warranty cards, logbooks, flyers, etc.

At block 430, another cutout is generated from the sheets of material for the cover. The cutout may be made from the same sheet or different sheet of material as the first cutout for the container, depending on amount of material provided. The cutout is shaped and sized for forming the cover—e.g., such as shown in FIG. 8. The cutout may be generated in any variety of manners as similarly described for the container. Once the cutout is formed, the cutout is folded to form the cover for the container, as represented by block 435. Once the cover is formed and all products and product materials inserted into the container, the cover is placed on the container, as represented by block 440.

In one embodiment, the methods include generating and folding a cutout for the ancillary container from a sheet of material. Again the sheet of material may be from the same or different sheet of material as used for the container and cover, depending on the amount of material. The ancillary container is shaped and sized to fit on the container. For example, the ancillary container may be shaped and sized to fit on the cover flap of the front compartment between the cover flap and the top wall of the cover, wherein a length and width of a contacting side of the ancillary container matches a length and width of the cover flap that the contacting side is disposed on. Once folded, products or product materials may be disposed in the ancillary container and then the ancillary container sealed or otherwise closed. The ancillary container may then be disposed in the container along with any of the additional products or product materials, and the cover placed over the container thereafter. For example, in one embodiment, analyte test strips are disposed in the ancillary container.

It should be appreciated that the packages, kits, and methods described herein may include graphical text or illustrations printed on the package. For example, instructional graphics, warning graphics, educational graphics, etc., may be imprinted on one or more walls of the container, cover, and/or ancillary container.

The packages, kits, and methods of the present disclosure create a user friendly product introduction, through interior organization. For example, in one embodiment, the package is a two-piece package including a container and cover, wherein a blood glucose monitoring device, lancets, a lancing device are organized in a front compartment of a container that is covered by the cover. The blood glucose meter, lancets, a lancing device may be viewable, for instance, upon removal of the cover from the container. Additional product materials, such as manuals and other relevant literature for example, may be stored in the rear compartment behind the front compartment and remain viewable above the shorter front compartment. Such organization may help reduce any fear, confusion, frustration, etc., that patients may experience when opening the package. Moreover, such organization enables patients to see most if not all of the products and materials within the package without taking it all out. Furthermore, the layout and organization enables a package that is smaller and compact, which may help reduce packing cost and bulkiness.

ADDITIONAL EXAMPLE EMBODIMENTS

As summarized above, in some aspects of the present disclosure, a package for an analyte monitoring device is provided. The package includes a container for containing an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container.

In one embodiment, the container includes a cover flap for the opening of the front compartment. In this way the front compartment may include various products and/or product materials and retain them within the front compartment.

In one embodiment, the container includes one or more dividing panels disposed within the front compartment to form subsections within the front compartment. In one embodiment, two dividing panels are disposed in the front compartment and form three subsections within the front compartment. Other number of dividing panels may be used in other embodiments.

In one embodiment, the container includes a retention element disposed in the rear compartment. For example, the retention element may be disposed on one or more walls of the container. In one embodiment, the retention element is formed as an inverse cutout on the rear wall and one of the sidewalls. The inverse cutout is bendable within the rear compartment and may be used to retain a product such as a test strip vial. In some instances, the inverse cutout is disposed in the rear compartment at a higher height than the front wall.

In one embodiment, the inner panel extends to the bottom wall. This provides separation between the front compartment and the rear compartment of the container. In other embodiments, the inner panel does not extend to the bottom wall such that the front compartment is connected to the rear compartment below the inner panel.

In one embodiment, the package includes a cover shaped and sized to fit over the top end of the container. The cover includes a top wall, a front wall, a rear wall, and two sidewalls extending from sides of the top wall to an open bottom end of the cover. The open bottom end of the cover receives the top end of the container. The cover lifts straight off the top end of the container when removed. In some instances, the open bottom end of the cover is curved and disposed higher than the bottom wall of the container when the cover is on the container. The curved bottom end of the cover may facilitate removal of the cover and may also help in identification of proper orientation of the package.

In one embodiment, the package includes an ancillary container. In some instances, the ancillary container is shaped and sized to fit on the cover flap of the front compartment between the cover flap and the top wall of the cover, wherein a length and width of a contacting side of the ancillary container matches a length and width of the cover flap that the contacting side is disposed on.

In one embodiment, the analyte is glucose or ketone body. The analyte monitoring device may be, for example, a glucose meter.

As summarized above, in some aspects of the present disclosure, an analyte monitoring kit is provided. The analyte monitoring kit includes a package for an analyte monitoring device, such as described above, as well as an analyte monitoring device disposed therein. For example, the package includes a container for containing an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container. The kit also includes an analyte monitoring device disposed in the container.

In one embodiment, the container includes a cover flap for the opening of the front compartment. In one embodiment, the container includes one or more dividing panels disposed within the front compartment to form subsections within the front compartment.

In one embodiment, the analyte monitoring device is disposed in the front compartment of the container. In other embodiments, the analyte monitoring device is disposed in the rear compartment.

In one embodiment, a lancing device is disposed in the container. In one embodiment, the lancing device is disposed in the front compartment—e.g., within a subsection of the front compartment.

In one embodiment, one or more lancets are disposed in the container. In one embodiment, the one or more lancets are disposed in the front compartment—e.g., within a subsection of the front compartment.

In one embodiment, a control solution is disposed in the container. In one embodiment, the control solution is disposed in the front compartment—e.g., within a subsection of the front compartment.

In one embodiment, literature related to the analyte monitoring device is disposed in the container. In one embodiment, literature related to the analyte monitoring device is disposed in the rear compartment.

In one embodiment, the container includes a retention element disposed in the rear compartment. In some instances, the retention element is an inverse cutout on the rear wall and one of the sidewalls, the inverse cutout foldable within the rear compartment. In some instances, the inverse cutout is disposed in the rear compartment at a higher height than the front wall.

In one embodiment, a strip vial is disposed in container. In one embodiment, a strip vial is disposed in the retention element.

In one embodiment, the inner panel extends to the bottom wall. In other embodiments, the inner panel does not extend to the bottom wall such that the front compartment is connected to the rear compartment below the inner panel.

In one embodiment, the analyte monitoring kit includes a cover shaped and sized to fit over the top end of the container. The cover includes a top wall, a front wall, a rear wall, and two sidewalls extending from sides of the top wall to an open bottom end of the cover. The open bottom end of the cover receives the top end of the container. In some instances, the open bottom end of the cover is curved and disposed higher than the bottom wall of the container when the cover is on the container.

In one embodiment, the analyte monitoring kit includes an ancillary container. In some instances, the ancillary container is shaped and sized to fit on the cover flap of the front compartment between the cover flap and the top wall of the cover, wherein a length and width of a contacting side of the ancillary container matches a length and width of the cover flap that the contacting side is disposed on. In one embodiment, the ancillary container includes analyte test strips.

In one embodiment, the analyte is glucose or ketone body. The analyte monitoring device may be, for example, a glucose meter.

In one embodiment, an insulin delivery device is provided in the container.

As summarized above, in some aspects of the present disclosure, methods of making a package for an analyte monitoring device are provided. The method includes providing one or more sheets of material, and generating a first cutout from one of the sheets of material. The shape of the first cutout is such that when folded in a plurality of locations, a container is formed. The method also includes folding the first cutout in a plurality of location to form a container for an analyte monitoring device. The container includes a bottom wall, a front wall, a rear wall, and two sidewalls extending from sides of the bottom wall to an open top end of the container. The front wall is shorter in height than the rear wall, and is on an opposite side of the bottom wall than the rear wall. The two sidewalls are on opposite sides of the bottom wall, and extend from the front wall to the rear wall. The package also includes an inner panel disposed between the front wall and the rear wall. A front compartment is formed between the inner panel and the front wall, and a rear compartment is formed between the inner panel and the rear wall. The opening of the rear compartment is at the top end of the container, and an opening of the front compartment is at the top end of the container.

In one embodiment, the methods include inserting an analyte monitoring device into the container.

In one embodiment, the container includes a cover flap for the opening of the front compartment. In one embodiment, the container includes one or more dividing panels disposed within the front compartment to form subsections within the front compartment.

In one embodiment, the analyte monitoring device is disposed in the front compartment of the container. In other embodiments, the analyte monitoring device is disposed in the rear compartment.

In one embodiment, the methods include inserting a lancing device into the container. In one embodiment, the lancing device is inserted into the front compartment.

In one embodiment, the methods include inserting one or more lancets into the container.

In one embodiment, the one or more lancets are inserted into the front compartment.

In one embodiment, the methods include inserting a control solution into the container. In one embodiment, the control solution is inserted into the front compartment.

In one embodiment, the methods include inserting literature related to the analyte monitoring device into the container. In one embodiment, the literature is inserted into the front compartment.

In one embodiment, the container includes a retention element disposed in the rear compartment. In some instances, the retention element is an inverse cutout on the rear wall and one of the sidewalls, the inverse cutout foldable within the rear compartment. In some instances, the inverse cutout is disposed in the rear compartment at a higher height than the front wall.

In one embodiment, the methods include inserting a strip vial into the container. In one embodiment, the strip vial is inserted into the retention element. In other embodiments, the strip vial is inserted into the front or rear compartment.

In one embodiment, the inner panel extends to the bottom wall. In other embodiments, the inner panel does not extend to the bottom wall such that the front compartment is connected to the rear compartment below the inner panel.

In one embodiment, the methods include generating a cutout wherein the shape of the cutout is such that when folded in a plurality of locations, an ancillary container is formed that is shaped and sized to fit on the container. In one embodiment, the methods include folding the cutout in a plurality of locations to form an ancillary container shaped and sized to fit on the cover flap of the front compartment between the cover flap and the top wall of the cover. A length and width of a contacting side of the ancillary container matches a length and width of the cover flap that the contacting side is disposed on.

In one embodiment, the methods include disposing an ancillary container on the container. In one embodiment, the ancillary container is disposed on the cover flap of the front compartment. Various products or product materials may be disposed in the ancillary container before the ancillary container is disposed in the container. For example, analyte test strips may be disposed in the ancillary container.

In one embodiment, the methods include generating a cutout wherein the shape of the cutout is such that when folded in a plurality of locations, a cover is formed. In one embodiment, the methods include folding the cutout in a plurality of locations to form a cover shaped and sized to fit over the top end of the container. The cover includes a top wall, a front wall, a rear wall, and two sidewalls extending from sides of the top wall to an open bottom end of the cover. The open bottom end of the cover receives the top end of the container.

In one embodiment, the methods include covering the container with the cover.

In one embodiment, the analyte is glucose or ketone body.

In one embodiment, the methods include inserting an insulin delivery device into the container. In one embodiment, the insulin delivery device is inserted into the front compartment.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present disclosure have been described with respect to various embodiments and specific examples herein, all of which may be made or carried out conventionally, it will be understood that the invention is entitled to protection within the full scope of the appended claims.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

That which is claimed is:

1. A package for an analyte monitoring device, comprising:
   a container for containing an analyte monitoring device, the container comprising:
   a bottom wall;
   a front wall, a rear wall, and two sidewalls extending from sides of the bottom wall to an open top end of the container, wherein the front wall is shorter in height than the rear wall, the front wall on an opposite side of the bottom wall than the rear wall, and wherein the two sidewalls are on opposite sides of the bottom wall, the two sidewalls extending from the front wall to the rear wall;
   an inner panel disposed between the front wall and the rear wall, wherein a front compartment is formed between the inner panel and the front wall, and wherein a rear compartment is formed between the inner panel and the rear wall; and
   a cover flap extending from the inner panel and comprising a foldable engagement tab that folds into the front compartment and engages with the front wall to close the front compartment;
   wherein an opening of the rear compartment is at the top end of the container, and
   wherein an opening of the front compartment is at the top end of the container.

2. The package of claim 1, wherein the container comprises one or more dividing panels disposed within the front compartment to form subsections within the front compartment.

3. The package of claim 1, wherein the container comprises a retention element disposed in the rear compartment.

4. The package of claim 3, wherein the retention element is an inverse cutout on the rear wall and one of the sidewalls, the inverse cutout foldable within the rear compartment.

5. The package of claim 4, wherein inverse cutout is disposed in the rear compartment at a higher height than the front wall.

6. The package of claim 1, wherein the inner panel extends to the bottom wall.

7. The package of claim 1, wherein the inner panel does not extend to the bottom wall such that the front compartment is connected to the rear compartment.

8. The package of claim 1, comprising:
   a cover shaped and sized to fit over the top end of the container, the cover comprising:
   a top wall; and
   a front wall, a rear wall, and two sidewalls extending from sides of the top wall to an open bottom end of the cover, wherein the open bottom end of the cover receives the top end of the container.

9. The package of claim 8, wherein the open bottom end of the cover is curved and disposed higher than the bottom wall of the container when the cover is on the container.

10. The package of claim 8, comprising:
    an ancillary container shaped and sized to fit on the cover flap of the front compartment between the cover flap and the top wall of the cover, wherein a length and width of a contacting side of the ancillary container matches a length and width of the cover flap that the contacting side is disposed on.

11. The package of claim 1, wherein the analyte monitoring device monitors glucose or ketone bodies.

12. The package of claim 1, wherein each sidewall has a first portion extending from the front wall and comprising a flat top edge and a second portion extending from the back wall, and wherein the first portion of each sidewall is shorter in height than the second portion of each sidewall.

13. The package of claim 12, wherein the second portion of each sidewall comprises a curved top edge.

14. An analyte monitoring kit, comprising:
a package for an analyte monitoring device, the package comprising:
a container for containing an analyte monitoring device, the container comprising:
a bottom wall;
a front wall, a rear wall, and two sidewalls extending from sides of the bottom wall to an open top end of the container, wherein the front wall is shorter in height than the rear wall, the front wall on an opposite side of the bottom wall than the rear wall, and wherein the two sidewalls are on opposite sides of the bottom wall, the two sidewalls extending from the front wall to the rear wall;
an inner panel disposed between the front wall and the rear wall, wherein a front compartment is formed between the inner panel and the front wall, and wherein a rear compartment is formed between the inner panel and the rear wall; and
a cover flap extending from the inner panel and comprising a foldable engagement tab that folds into the front compartment and engages with the front wall to close the front compartment;
wherein an opening of the rear compartment is at the top end of the container, and
wherein an opening of the front compartment is at the top end of the container; and
an analyte monitoring device disposed in the container.

15. The analyte monitoring kit of claim 14, wherein the container comprises:
one or more dividing panels disposed within the front compartment to form subsections within the front compartment.

16. The analyte monitoring kit of claim 14, wherein the analyte monitoring device is disposed in the front compartment of the container.

17. The analyte monitoring kit of claim 14, wherein a lancing device is disposed in the front compartment.

18. The analyte monitoring kit of claim 14, wherein one or more lancets are disposed in the front compartment.

19. The analyte monitoring kit of claim 14, wherein control solution is disposed in the front compartment.

20. The analyte monitoring kit of claim 14, wherein literature related to the analyte monitoring device is disposed in the rear compartment.

21. The analyte monitoring kit of claim 14, wherein the container comprises:
a retention element disposed in the rear compartment.

22. The analyte monitoring kit of claim 21, wherein the retention element is an inverse cutout on the rear wall and one of the sidewalls, the inverse cutout foldable within the rear compartment.

23. The analyte monitoring kit of claim 22, wherein inverse cutout is disposed in the rear compartment at a higher height than the front wall.

24. The analyte monitoring kit of claim 21, wherein a strip vial is disposed in the retention element.

25. The analyte monitoring kit of claim 14, wherein the inner panel extends to the bottom wall.

26. The analyte monitoring kit of claim 14, wherein the inner panel does not extend to the bottom wall such that the front compartment is connected to the rear compartment.

27. The analyte monitoring kit of claim 14, comprising:
a cover shaped and sized to fit over the top end of the container, the cover comprising:
a top wall; and
a front wall, a rear wall, and two sidewalls extending from sides of the top wall to an open bottom end of the cover, wherein the open bottom end of the cover receives the top end of the container.

28. The analyte monitoring kit of claim 27, comprising:
an ancillary container shaped and sized to fit on the cover flap of the front compartment between the cover flap and the top wall of the cover, wherein a length and width of a contacting side of the ancillary container matches a length and width of the cover flap that the contacting side is disposed on.

29. The analyte monitoring kit of claim 28, wherein the ancillary container comprises analyte test strips.

30. The analyte monitoring kit of claim 14, wherein the analyte monitoring device monitors glucose or ketone bodies.

31. The analyte monitoring kit of claim 14, wherein an insulin delivery device is provided in the container.

32. The analyte monitoring kit of claim 14, wherein each sidewall has a first portion extending from the front wall and comprising a flat top edge and a second portion extending from the back wall, and wherein the first portion of each sidewall is shorter in height than the second portion of each sidewall.

33. The analyte monitoring kit of claim 32, wherein the second portion of each sidewall comprises a curved top edge.

* * * * *